United States Patent [19]

Crouse et al.

[11] Patent Number: 4,944,795
[45] Date of Patent: Jul. 31, 1990

[54] 3-BUTENANILIDES

[75] Inventors: Gary D. Crouse, Indianapolis; Jeffery D. Webster, New Palestine, both of Ind.

[73] Assignee: Eli Lilly and Company, Indianapolis, Ind.

[21] Appl. No.: 428,557

[22] Filed: Oct. 30, 1989

[51] Int. Cl.$^5$ .................... A01N 31/14; C07C 233/08
[52] U.S. Cl. .......................................... 71/98; 71/103; 71/105; 71/118; 558/414; 362/598; 564/207
[58] Field of Search ................... 564/207; 71/118, 98, 71/103

[56] References Cited

U.S. PATENT DOCUMENTS

| | | | |
|---|---|---|---|
| H327 | 9/1987 | DiSanzo et al. | 564/207 |
| 2,368,195 | 1/1945 | Britton et al. | 564/207 |
| 4,014,679 | 3/1977 | Perronnet et al. | 71/118 |
| 4,014,679 | 3/1977 | Perronnet et al. | 564/207 |
| 4,902,334 | 2/1990 | Azuma et al. | 71/88 |

FOREIGN PATENT DOCUMENTS

| | | | |
|---|---|---|---|
| 2830351 | 1/1980 | Fed. Rep. of Germany | 564/207 |
| 1141183 | 1/1969 | United Kingdom | 71/98 |

OTHER PUBLICATIONS

Derwent 67-8976G.
Derwent 70-92057R.
Derwent 74-72659V.
Derwent 80-5778C.
Derwent 81-90318D.
Derwent 86-190807.
Derwent 70-84562R.
Derwent 75-22413W.
Derwent 75-70701W.
Haberle et al., "Acylanilides", CA 93: 2631 p, p. 673, 1980.

Primary Examiner—Glennon H. Hollrah
Attorney, Agent, or Firm—Donald R. Stuart; Leroy Whitaker

[57] ABSTRACT

3-Butenanilides of the formula (1)

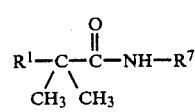

(1)

$$R^1-C-C-NH-R^7$$
with CH$_3$, CH$_3$ on middle carbon wherein R$^1$ is

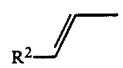

(a)
(E)
where R$^2$ is F, Cl, Br, I, SCH$_3$, or OCH$_3$, -continued

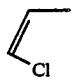

(b)
(Z)

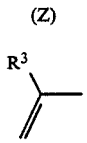

(c)
where R$^3$ is F, Cl, or Br,

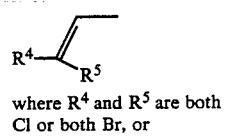

(d)
where R$^4$ and R$^5$ are both Cl or both Br, or

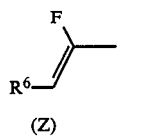

(e)
(Z)
where R$^6$ is F, Cl, or Br; and R$^7$ is (a)
where R$^8$ is H, F, Cl, Br, I, SCF$_3$, or CF$_3$,

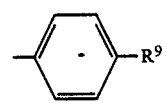

(b)
where R$^9$ is F, Cl, Br, I, CN, SCF$_3$, SOCF$_3$, SO$_2$CF$_3$, (C$_1$-C$_3$) alkyl, halo (C$_1$-C$_3$) alkyl, (C$_1$-C$_3$) alkoxy, halo (C$_1$-C$_3$) alkoxy, phenoxy, substituted phenoxy;

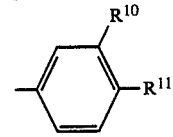

(c)
where R$^{10}$ and R$^{11}$ are independently F, Cl, Br, SCH$_3$, or CF$_3$; or

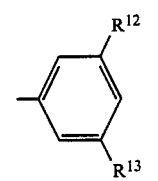

(d)
where R$^{12}$ and R$^{13}$ are both F or both Cl are broad spectrum herbicides. Also disclosed are herbicidal compositions containing a compound of formula (1) as active ingredient, and herbicidal methods. Novel but-3-enoic acid intermediates useful in preparation of formula (1) compounds are also disclosed.

17 Claims, No Drawings

3-BUTENANILIDES

SUMMARY OF THE INVENTION

This invention provides compounds of the formula (1)

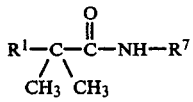

wherein $R^1$ is (a)
(E)
where $R^2$ is F, Cl, Br, I, $SCH_3$, or $OCH_3$, (b)
(Z)

(c)
where $R^3$ is F, Cl, or Br, (d)
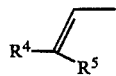
where $R^4$ and $R^5$ are both Cl or both Br, or (e)
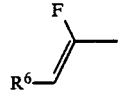
(Z)
where $R^6$ is F, Cl, or Br; and $R^7$ is (a)
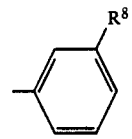
where $R^8$ is H, F, Cl, Br, I, $SCF_3$, or $CF_3$, (b)
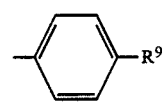
where $R^9$ is F, Cl, Br, I, CN, $SCF_3$, $SOCF_3$, $SO_2CF_3$, ($C_1$-$C_3$) alkyl, halo ($C_1$-$C_3$) alkyl, ($C_1$-$C_3$) alkoxy, halo ($C_1$-$C_3$) alkoxy, phenoxy, substituted phenoxy;

(c)
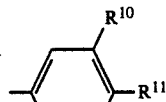
where $R^{10}$ and $R^{11}$ are independently F, Cl, Br, $SCH_3$, or $CF_3$; or (d)
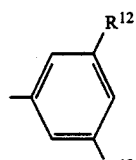
where $R^{12}$ and $R^{13}$ are both F or both Cl.

Compounds of formula (1) are useful as herbicides. Compositions containing these compounds are also disclosed.

The invention also provides novel but-3-enoic acids of the formula (2)

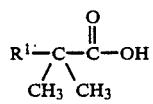

where $R^1$ is as defined in formula (1), which are useful in preparing compounds of formula (1).

DETAILED DESCRIPTION OF THE INVENTION

In the above formulae, ($C_1$-$C_3$) alkyl represents a straight or branched chain alkyl chain having from one to three carbon atoms.

($C_1$-$C_3$) alkoxy represents a straight or branched alkoxy chain having from one to three carbon atoms.

($C_1$-$C_3$) haloalkoxy represents a ($C_1$-$C_3$) alkoxy group bearing one or more F, Cl, or Br groups.

Substituted phenoxy represents a phenoxy group bearing one or more F, Cl, or Br groups.

While all of the compounds of formula (1) are useful herbicides, certain classes are preferred for reasons of greater efficacy or ease of synthesis, viz:

(a) compounds of formula (1) wherein $R^1$ is

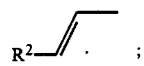 ;

(b) compounds of class (a) wherein $R^2$ is Cl or Br, particularly Cl;

(c) compounds of formula (1) wherein $R^7$ is 4-fluorophenyl, 4-chlorophenyl, or 4-bromophenyl;

(d) compounds of formula (1) wherein $R^7$ is 3-fluorophenyl, 3-chlorophenyl, or 3-bromophenyl;

(e) compounds of formula (1) wherein $R^7$ is 3,4-difluorophenyl, 3,5-difluorophenyl, 3-chloro-4-fluorophenyl, or 3-fluoro-4-chlorophenyl; and (f) compounds of formula (1) wherein $R^7$ is 4-(trifluoromethyl)phenyl, 4-[(trifluoromethyl)thio]phenyl, or 4-[(trifluoromethyl)sulfinyl]phenyl.

The most preferred compound is (E)-4-chloro-N-(4-chlorophenyl)-2,2-dimethyl-3-butenamide.

GENERAL PREPARATION METHODS

The compounds of formula (1) may generally be prepared by condensing a but-3-enoic acid derivative of formula (2)

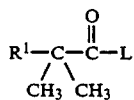

where $R^1$ is as defined above and L is a good leaving group, such as $C_1$–$C_4$ alkoxy, halogen, imidazoyl, or

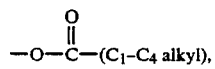

with an aniline of the formula (3)

where $R^7$ is as defined above. The preferred leaving group L is Cl. This reaction can be carried out by combining the carboxylic acid derivative with about an equimolar quantity of the aniline in a mutual solvent, such as chloroform. When L is halogen, a base is advantageously used to act as an acid scavenger. Commonly used bases include pyridine, triethylamine, sodium carbonate, and related bases.

Preparation of the required but-3-enoic acid starting materials is described in detail in the following examples.

COMPOUNDS 1–49

The following compounds are prepared by the general procedure described above. The melting point of each compound is given. In addition, although the data has not been included, each compound was fully characterized by NMR, IR, mass spectra, and combustion analysis.

Detailed descriptions for preparation of compounds 7, 19, 32–38, 41–44, and 46–49 follow the tabular listing. Detailed descriptions for preparation of the but-3-enoic acid starting materials used in these syntheses are also given.

| COMPOUND NUMBER | COMPOUND | M.P. |
| --- | --- | --- |
| 1 | (E)-4-bromo-N-(4-cyanophenyl)-2,2-dimethyl-3-butenamide | 96–97° C. |
| 2 | (E)-4-bromo-N-(4-phenoxyphenyl)-2,2-dimethyl-3-butenamide | 102° C. |
| 3 | (E)-4-bromo-N-phenyl-2,2-dimethyl-3-butenamide | 104° C. |
| 4 | (E)-4-bromo-N-[4-(trifluoromethyl)phenyl]-2,2-dimethyl-3-butenamide | 129–131° C. |
| 5 | (E)-4-bromo-N-[3-(trifluoromethyl)phenyl]-2,2-dimethyl-3-butenamide | 73–75° C. |
| 6 | (E)-4-bromo-N-(3-chlorophenyl)-2,2-dimethyl-3-butenamide | 84–85° C. |
| 7 | (E)-4-bromo-N-(4-chlorophenyl)-2,2-dimethyl-3-butenamide | 125–127° C. |
| 8 | (E)-4-bromo-N-(3,4-dichlorophenyl)-2,2-dimethyl-3-butenamide | 113–115° C. |
| 9 | (E)-4-bromo-N-(4-methoxyphenyl)-2,2-dimethyl-3-butenamide | 104–105° C. |
| 10 | (E)-4-bromo-N-(4-methylphenyl)-2,2-dimethyl-3-butenamide | 93–94° C. |
| 11 | (E)-4-bromo-N-(4-bromophenyl)-2,2-dimethyl-3-butenamide | 126–127° C. |
| 12 | (E)-4-bromo-N-(4-fluorophenyl)-2,2-dimethyl-3-butenamide | 104–105° C. |
| 13 | (E)-4-bromo-N-(4-iodophenyl)-2,2-dimethyl-3-butenamide | 128–130° C. |
| 14 | (E)-4-bromo-N-(3,4-dibromophenyl)-2,2-dimethyl-3-butenamide | 100–101° C. |
| 15 | (E)-N-(4-bromophenyl)-4-chloro-2,2-dimethyl-3-butenamide | 97–98° C. |
| 16 | (E)-4-chloro-2,2-dimethyl-N-[4-(trifluoromethyl)phenyl]-3-butenamide | 119–122° C. |
| 17 | (E)-4-chloro-2,2-dimethyl-N-(4-phenoxyphenyl)-3-butenamide | 90–93° C. |
| 18 | (E)-4-chloro-N-(4-chloro-3-fluorophenyl)-2,2-dimethyl-3-butenamide | 103–104° C. |
| 19 | (E)-4-chloro-N-(4-chlorophenyl)-2,2-dimethyl-3-butenamide | 110–111° C. |
| 20 | (E)-4-chloro-2,2-dimethyl-N-[4-[(trifluoromethyl)thio]phenyl]-3-butenamide | 107–109° C. |
| 21 | (E)-4-chloro-2,2-dimethyl-N-[4-[(trifluoromethyl)sulfinyl]phenyl]-3-butenamide | 91–92° C. |
| 22 | (E)-4-chloro-2,2-dimethyl-N-[4-[(trifluoromethyl)sulfonyl]phenyl]-3-butenamide | 140° C. |
| 23 | (E)-4-chloro-N-(3,5-difluorophenyl)-2,2-dimethyl-3-butenamide | 70–71° C. |
| 24 | (E)-4-chloro-N-[4-(4-bromophenoxy)phenyl]-2,2-dimethyl-3-butenamide | 84–85° C. |
| 25 | (E)-N-[4-bromo-3-(trifluoromethyl)phenyl]-4-chloro-2,2-dimethyl-3-butenamide | 79–80° C. |
| 26 | (E)-4-chloro-N-(3,4-dichlorophenyl)-2,2-dimethyl-3-butenamide | 104° C. |
| 27 | (E)-4-chloro-N-(3-chloro-4-fluorophenyl)-2,2-dimethyl-3-butenamide | 100–101° C. |
| 28 | (E)-4-chloro-N-[4-chloro-3-(trifluoromethyl)phenyl]-2,2-dimethyl-3-butenamide | 84–85° C. |
| 29 | (E)-4-chloro-2,2-dimethyl-N-[4-(4-chlorophenoxy)phenyl]-3-butenamide | 89–90° C. |
| 30 | N-(4-bromophenyl)-3-chloro-2,2-dimethyl-3-butenamide | 104–109° C. |
| 31 | (E)-N-(4-chlorophenyl)-2,2-dimethyl-4-(phenylthio)-3-butenamide | 100–102° C. |
| 32 | (E)-N-(4-chlorophenyl)-3,4-difluoro-2,2-dimethyl-3-butenamide | 100° C. |
| 33 | (Z)-N-(4-chlorophenyl)-3,4-difluoro-2,2-dimethyl-3-butenamide | 99° C. |
| 34 | (Z)-4-chloro-N-(4-chlorophenyl)-2,2-dimethyl-3-butenamide | 127–128° C. |
| 35 | (E)-N-(4-chlorophenyl)-4-iodo-2,2-dimethyl-3-butenamide | 145–146° C. |
| 36 | 3-bromo-2,2-dimethyl-N-[3-(trifluoromethyl)phenyl]-3-butenamide | 69° C. |
| 37 | 3-bromo-2,2-dimethyl-N-[3-[(trifluoromethyl)thio]phenyl]-3-butenamide | 68–69° C. |
| 38 | 3-bromo-N-(3-chlorophenyl)-2,2-dimethyl-3-butenamide | 70–72° C. |
| 39 | (Z)-4-chloro-N-[3-(trifluoromethyl)phenyl]-2,2-dimethyl-3-butenamide | 85–87° C. |
| 40 | (Z)-4-chloro-N-(3-chlorophenyl)-2,2-dimethyl-3-butenamide | 127–129° C. |
| 41 | (E)-N-(4-chlorophenyl)-2,2-dimethyl-4-(methylthio)-3-butenamide | 105–106° C. |
| 42 | (E)-N-(4-chlorophenyl)-4-methoxy-2,2-dimethyl-3-butenamide | 93° C. |
| 43 | N-(4-chlorophenyl)-2,2-dimethyl-3-fluoro-3-butenamide | 75–76° C. |
| 44 | (Z)-4-bromo-N-(4-chlorophenyl)-2,2-dimethyl-3-fluoro-3-butenamide | 131–133° C. |

| COMPOUND NUMBER | COMPOUND | M.P. |
|---|---|---|
| 45 | (Z)-4-bromo-N-(3,4-dichlorophenyl)-2,2-dimethyl-3-fluoro-3-butenamide | 120–122° C. |
| 46 | (Z)-N-(4-chlorophenyl)-4-chloro-3-fluoro-2,2-dimethyl-3-butenamide | 118–121° C. |
| 47 | 4,4-dibromo-N-(4-chlorophenyl)-2,2-dimethyl-3-butenamide | 104° C. |
| 48 | (E)-N-(4-bromophenyl)-4-fluoro-2,2-dimethyl-3-butenamide | 87–90° C. |
| 49 | 4,4-dichloro-N-(4-chlorophenyl)-2,2-dimethyl-3-butenamide | 131–134° C. |

EXAMPLE 1

(E)-4-Chloro-2,2-dimethylbut-3-enoic acid

A five liter four neck round bottom flask equipped with thermometer, cold bath, mechanical stirrer and inlet tube for subsurface gas introduction was charged with 470 g of ethyl 2,2-dimethylbut-3-enoate (prepared according to the procedure of J. L. Hermann, G. R. Kiecgykowski, and R. H. Schessinger, *Tetr. Lett.*, 2425 (1973)) and 2500 mL of chloroform. The solution was cooled to 0° C. and chlorine was bubbled into the solution at a rate that kept the internal temperature below 10° C. (3 hours total addition time). After removal of solvent, the residue (703 g) was taken up in 2500 mL of DMF and cooled to −5° C. Potassium t-butoxide (636 g) was added to the stirred solution at a rate such that the temperature remained below 0° C. (2.3 hours total addition time). After the addition was complete, the solution was stirred an additional 1 hour, then poured onto 3 L of ice and water and extracted into 2×2 L of hexane. The combined hexane fraction was washed with 2×200 mL of saturated brine solution, dried over Na$_2$SO$_4$ and stripped to give 422 g of (E)-ethyl-4-chloro-2,2-dimethylbut-3-enoate an oil. This was then added over ½ hour to a stirred, cooled (−5° C.) solution of KOH (280 g) in methanol (1 L). Stirring was continued for 16 hours at ambient temperature, then the solution was poured into 3 L of ice water and extracted with 2×2 L of ether. The aqueous layer was then acidified to pH 2 using concentrated HCl, and extracted with 2×2 L of ether. The combined acid extracts were dried over Na$_2$SO$_4$ and stripped of solvent to give 222 g of an oil.

The nonacidic extract (125 g) consisted primarily of the corresponding t-butyl ester; refluxing this ester with an equivalent volume of trifluoroacetic acid for 4 hours and subsequent concentration in vacuo resulted in the isolation of an additional 80 g of chlorovinyl acid.

EXAMPLE 2

(E)-4-chloro-N-(4-chlorophenyl)-2,2-dimethyl-3-butenamide (Compound 19)

and 3-chloro-N-(4-chlorophenyl)-2,2-dimethyl-3-butenamide 4-chloro-2,2-dimethylbut-3-enoic acid (38.5 g) was treated with 35 g of thionyl chloride with heating on a steam bath for 1 hour. After cooling and removal of volatiles in vacuo, the acid chloride was added dropwise to a cooled (5° C.) solution of p-chloroaniline (33.5 g) and pyridine (50 mL) in 150 mL of chloroform. After the solution was stirred an additional 1 hour at ambient temperature, it was poured onto ice and excess concentrated HCl. The organic layer was removed, washed with brine solution and concentrated to give after recrystallization from chloroform/hexane 43.8 g of the title compound (Compound 19) as a solid, m.p. 108° C.

The mother liquor from the above reaction (18 g) was chromatographed through silica gel to furnish 9 g of additional 4-chloro isomer along with 0.5 g of 3-chloro-N-(4-chlorophenyl)-2,2-dimethyl-3-butenamide, m.p. 84°–86° C.

EXAMPLE 3

(E)-4-bromo-2,2-dimethylbut-3-enoic acid

Bromine (256 g) was added dropwise over two hours to a stirred solution of ethyl 2,2-dimethylbut-3-enoate (284 g) in 3 L of hexane with cooling to maintain ambient temperature. Removal of solvent gave 481 g of the dibromide as an oil. This was taken up in 1200 mL of DMF and stirred at −10° to 0° C. while potassium t-butoxide (198 g) was added in portions over 45 minutes. Stirring was continued for one hour after addition was complete, then the solution was poured into ice water and extracted with 1.5 L of hexane. The combined organic layer was washed with 2×250 mL of a saturated brine solution, then dried and stripped of solvent to afford 257.4 g of a reddish oil. This oil then added dropwise to a 0° C. solution of potassium hydroxide (66 g) in 600 mL of methanol. The solution was stirred 16 hours, then poured onto ice water and extracted with 2×1 L of ether. The aqueous layer was acidified with concentrated HCl, then extracted with 2×1 L of ether. The combined acid extract was washed with water, dried and stripped of solvent to give 142 g of (E)-4-bromo-2,2-dimethylbut-3-enoic acid as a light red oil which solidified on standing, m.p. 30° C.

EXAMPLE 4

4-Bromo-N-(4-chlorophenyl)-2,2-dimethyl-3-butenamide (Compound 7)

4-Bromo-2,2-dimethylbut-3-enoic acid (29.8 g) was treated with 22 mL of thionyl chloride with heating on a steam bath for one hour. After cooling and removal of volatiles in vacuo, the acid chloride was added dropwise to a cooled (5° C.) solution of p-chloroaniline (33.5 g) in pyridine (50 mL). Stirring was continued at ambient temperature overnight, and the solution was then concentrated at reduced pressure. The residue was taken up in chloroform and washed with water and dilute hydrochoric acid. The solution was then dried, treated with activated charcoal, filtered and stripped of solvent to afford a solid. Recrystallization from chloroform/hexanes gave 33 g of the title compound (compound 7), m.p. 134°–135° C.

EXAMPLE 5

(Z and E)-3,4-difluoro-2,2-dimethylbut-3-enoic acids

Lithium diisopropyl amide (0.142 mole) was prepared by adding n-butyllithium (65 mL of 2.2M, 0.142 mole) to a stirred solution of diisopropyl amine (14.3 g, 0.142 mole) in 200 mL of dry tetrahydrofuran at −50° C. Ethyl isobutyrate (14.9 g, 0.129 mole) was then added dropwise to the stirred cold solution. The solution was stirred an additional 1 hour at −60° C., then hexamethylphosphoramide (HMPA: 23.1 g, 0.129 mole) was added in one portion.

In a separate flask, 1,2-dibromo-1,1,2-trifluoroethane (34.4 g, 0.142 mol) was added dropwise to a stirred slurry of powdered zinc (16.9 g, 0.258 g at.) in 75 mL of absolute ethanol. The resulting gaseous 1,1,2-trifluoroethylene was bubbled through the anionic solution at −65° C. Upon completion of the addition, the mixture was allowed to warm slowly to −15° C. and was then poured into a solution of ice and concentrated HCl. The solution was extracted with 2×100 mL of ether and the organic fraction dried and evaporated at 0° C. to afford 18.7 g of an oil. Distillation at 10 mm Hg yielded a fraction (14.3 g) boiling at 20°–75° C., which contained some solvent as well as the desired esters. Fractional distillation at 10 mm Hg furnished 6 g of ethyl 3,4-difluoro-2,2-dimethylbut-3-enoate as a colorless oil, bp. 38°–41° C., consisting of Z and E isomers in a 9:1 ratio. A solution of the (Z and E) esters (11 g) in 50 mL of ethanol was stirred at ambient temperature with 7.4 g of sodium hydroxide for 60 hours. The material was then diluted with 100 mL of water, extracted with ether and the aqueous layer acidified and again extracted with 2×100 mL of ether. The organic layer was dried and concentrated to afford 8.1 g of (Z and E) 3,4-difluoro-2,2-dimethylbut-3-enoic acids, contaminated with a small amount of isobutyric acid and 3,3,4-trifluorodimethylbutyric acid.

EXAMPLE 6

(E)-N-(4-Chlorophenyl)-3,4-difluoro-2,2-dimethyl-3-butenamide (Compound 32)

and (Z)-N-(4-Chlorophenyl)-3,4-difluoro-2,2-dimethyl-3-butenamide (Compound 33)

The mixture of acids produced in Example 5 was treated with 7.9 ml of thionyl chloride with heating on a steam bath for ½ hour. Volatiles were removed at 0° C., and the crude acid chlorides were added dropwise to p-chloroaniline (6.8 g) in 50 ml of pyridine. The solution was allowed to stir at ambient temperature for 1.5 hours, then heated briefly on a steam bath. The solution was then allowed to cool, then poured into ice and water, extracted with 2×100 mL of ether and the organic layer washed with dilute HCl until the washings remained acidic. Drying and removal of solvent afforded an oil which was subjected to silica gel chromatography, using gradient elution from 25:75 ethyl acetate:petroleum ether to 100% ethyl acetate. From this were isolated (E)-N-(4-chlorophenyl)-3,4-difluoro-2,2-dimethyl-3-butenamide (Compound 32) (4.7 g, m.p. 100° C.), (Z)-(4-chlorophenyl)-3,4-difluoro-2,2-dimethyl-3-butenamide (0.68 g, m.p. 99° C.) (Compound 33) and p-chlorophenyl 3,4,4-trifluoro-2,2-dimethylbutyric acid anilide (0.03 g).

EXAMPLE 7

(Z)-4-chloro-2,2-dimethylbut-3-enoic acid and 4,4-dichloro-2,2-dimethylbut-3-enoic acid Butyllithium (80 mL of 2.3M) was added to 26 mL of diisopropylamine in 200 mL of ethyl ether at −5° C., and the solution was then cooled to −50° C. Ethyl isobutyrate (15 g) was added dropwise over ½ hour, followed by chloral (19.2 g), dropwise over ½ hour. The solution was stirred an additional 2 hours, then poured onto ice, extracted into ether, washed with 1N HCl until the washings remained acidic, then dried over MgSO₄, filtered and concentrated in vacuo. The residue was distilled, collecting 20.3 g of ethyl 4,4,4-trichloro-3-hydroxy-2,2-dimethylbutanoate (b.p. 126°–127° C., 10 mm Hg).

The trichlorohydroxyester (20.3 g) was placed in a 500 mL flask with 150 mL of glacial acetic acid and 25.5 g of powdered zinc. The mixture was heated at reflux for 48 hours, then filtered, cooled, diluted with 250 mL of water and extracted with 2×200 mL of ether. The organic layer was washed repeatedly with 0.5N NaOH until the aqueous extracts remained alkaline. The organic layer was then dried over MgSO₄, filtered and concentrated carefully in vacuo to furnish 10.8 g of an oil. Distillation furnished 6.3 g of a fraction boiling at 58°–85° C., which was predominantly ethyl (Z)-4-chloro-2,2-dimethyl-3-butenoate, but which also contained a small percentage of the (E) isomer. The pot residue (2.6 g) consisted of the 4-4-dichlorovinyl ester, which was used without further purification.

The (Z)-chloro ester (6.3 g) was treated with 6.4 g of potassium hydroxide in ethanol overnight. Acidification and extraction into ether followed by drying and concentration in vacuo furnished 5.4 g of (Z)-4-chloro-2,2-dimethylbut-3-enoic acid.

The 4,4-dichlorovinyl ester (2.6 g) was treated with 2.1 g of potassium hydroxide in 25 mL of ethyl alcohol, at the reflux temperature overnight. The solution was cooled, extracted with ether and the aqueous layer acidified with 1N HCl. The product was then extracted into ether, washed with brine, dried over MgSO₄, filtered and concentrated in vacuo to give 1.89 g of 4,4-dichloro-2,2-dimethylbut-3-enoic acid.

EXAMPLE 8

(Z)-4-chloro-N-(4-chlorophenyl)-2,2-dimethyl-3-butenamide (Compound 34)

One gram of (Z)-4-chloro-2,2-dimethylbut-3-enoic acid was converted to the corresponding p-chloroanilide according to the procedure described in Example 1. Chromatography (silica gel, eluting with 25:75 ethyl acetate-hexanes) furnished 1.5 g of (Z)-4-chloro-N-(4-chlorophenyl)-2,2-dimethyl-3-butenamide; m.p. 127°–128° C.

EXAMPLE 9

(E)-N-(4-chlorophenyl)-4-iodo-2,2-dimethyl-3-butenamide (Compound 35)

p-Chlorophenyl isocyanate (21.08 g) and the morpholinoenamine of isobutyraldehyde (38.7 g) were stirred together in a 100 mL round bottom flask. After an initial exotherm, the solution was allowed to stir at ambient temperature overnight. The excess enamine was then removed in vacuo at 60° C., and the residue was taken up in ether and hexane added. The material was filtered to remove an unwanted urea side product, then the filtrate was washed with dilute HCl, and additional ether was added to redissolve some precipitated product. The organic layer was then dried and concentrated in vacuo to give a solid. Recrystallization furnished 21 g of N-(4-chlorophenyl)-2,2-dimethyl-3-oxopropanamide, m.p. 99°–100° C.

To a stirred suspension of chromous chloride (3.3 g) in 75 mL of dry THF was added a solution of iodoform (3.5 g) and N-(4-chlorophenyl)-2,2-dimethyl-3-oxopropanamide (1 g) in 25 mL of THF, dropwise over 10 minutes. The solution was allowed to stir an additional 1.5 hour, then poured into 100 g of ice water and extracted into ether. The organic phase was dried, filtered and evaporated, and the residue was filtered through a small silica gel column, eluting with ether, to remove chromium residues. The title product (0.55 g) was isolated as a solid, m.p. 145°–146° C.

EXAMPLE 10

3-Bromo-2,2-dimethylbut-3-enoic acid

Ethyl 3,4-dibromo-2,2-dimethylbutanoate (6.3 g), prepared as described in Example 3 above, was treated with 3.6 g of potassium hydroxide in 50 mL of 4:1 methanol:water and stirred 16 hours at ambient temperature. The solution was diluted with 100 mL of water and extracted with ether. The organic layer was washed with a saturated brine solution, dried and concentrated in vacuo to give 1.7 g of methyl 3-bromo-2,2-dimethylbut-3-enoate as an oil.

Methyl 3-bromo-2,2-dimethylbut-3-enoate (7.4 g) was stirred in 1:1 methanol:water containing 3 g of sodium hydroxide at the reflux temperature for two hours, then the solution was cooled, acidified with 1N HCl and extracted with ether. The organic layer was dried and concentrated to furnish 5.5 g of 3-bromo-2,2-dimethylbut-3-enoate acid as an oil.

EXAMPLES 11–13

3-Bromo-2,2-dimethylbut-3-enoic acid was converted to the following 3-butenamides using the conditions described in Example 2:

11. 3-Bromo-2,2-dimethyl-N-[3-(trifluoromethyl)-phenyl]-3-butenamide (Compound 36), m.p. 69° C.

12. 3-Bromo-2,2-dimethyl-N-[3-[(trifluoromethyl)thio]phenyl]-3-butenamide (Compound 37), m.p. 68°–69° C.

13. 3-Bromo-N-(3-chlorophenyl)-2,2-dimethyl-3-butenamide (Compound 38), m.p. 70°–72° C.

EXAMPLE 14

2,2-Dimethyl-4-methylthio-3-butenoic acid

A solution of methanethiol (8 g) in CCl$_4$ was stirred and treated dropwise at $-25°$ C. with bromine (26.6 g). Ethyl 2,2-dimethyl-3-butenoate (23 g) was then added dropwise at that temperature over two hours. Following the addition, the solution was allowed to warm to room temperature, then concentrated in vacuo. NMR showed near complete conversion to the 4-bromo-3-methylthio ester (38 g). The residual oil was then heated one hour on a steam bath to effect conversion to the thermodynamically favored 3-bromo-4-methylthio ester. This material was then dissolved in 50 mL of DMF and treated with 26 g of DBU. The solution was heated briefly on a steam bath, then was allowed to cool and worked up by pouring into water, extracting with 2×200 mL of ether, drying and concentrating. The residual oil (24.75 g) was hydrolyzed by stirring overnight in a solution of 50 mL of ethanol, 15 mL of water and 7.8 g of sodium hydroxide. Acidification with 1N HCl and extraction into ether followed by drying and concentration furnished a solid which was recrystallized from ether/hexane to give 13.5 g of 2,2-dimethyl-4-methylthio-3-butenoic acid, m.p. 49°–51° C.

EXAMPLE 15

(E)-N-(4-Chlorophenyl)-2,2-dimethyl-4-(methylthio)-3-butenamide (Compound 41)

A solution of 0.5 g of 2,2-dimethyl-4-methylthio-3-butenoic acid in 20 mL of ethyl acetate was treated with 0.6 g of carbonyldiimidazole, and the solution was heated for 10 minutes at reflux. After the solution had cooled, 0.65 g of p-chloroaniline was added and heating continued for 16 hours. The solution was then cooled, poured into water and extracted into ethyl acetate. The organic layer was washed with 50 mL of 1N HCl, dried over MgSO$_4$, and concentrated. The residual solid was recrystallized from CHCl$_3$/hexane to give 0.27 g of N-(4-chlorophenyl)-2,2-dimethyl-4-(methylthio)-3-butenamide, m.p. 105°–106° C.

EXAMPLE 16

(E)-4-methoxy-2,2-dimethylbut-3-enoic acid

A solution of 40 g of ethyl 4-chloro-2,2-dimethylbut-3-enoate in 150 mL of anhydrous methanol was treated with 50 g of N-bromosuccinimide. Triethylamine (0.5 mL) was then added to initiate the reaction, which warmed to 40° to 50° C. After the reaction was complete, the solution was concentrated in vacuo, triturated with CCl$_4$ and filtered to remove succinimide. The filtrate was concentrated to yield 74 g of an oil. The oil was added to 120 mL of DMF and stirred at 5° C. while 60 g of potassium t-butoxide was added in portions over two hours. Following the addition, the solution was poured onto 300 g of ice, then extracted into ether, dried over MgSO$_4$, concentrated in vacuo, and distilled to provide 39 g of (E) ethyl 4-methoxy-2,2-dimethylbut-3-enoate as a colorless oil, b.p. 67°–74° C. (10 mm Hg).

A solution of 15 g of the ester in 40 mL of 3:1 ethanol/water was treated with 10 mL of 50% aqueous sodium hydroxide. The solution was allowed to stir 20 hours, then concentrated to ¼ volume, extracted with ether, acidified to pH 1 with 1N HCl and re-extracted with 2×100 mL of ether. The organic layer was dried and concentrated in vacuo to yield 9 g of (E)-4-methoxy-2,2-dimethylbut-3-enoic acid as a colorless oil which solidified on storage in a freezer.

EXAMPLE 17

N-(4-chlorophenyl)-4-methoxy-2,2-dimethyl-3-butenamide (Compound 42)

A solution of 3 g of the acid in 15 mL of DMF was treated with 3.71 g of carbonyldiimidazole. After 45 minutes, p-chloroaniline (2.9 g) was added and the solution was heated on a steam bath overnight. After the solution had cooled, it was poured into 100 mL of water, extracted with ether, and the organic layer washed with 1N HCl, dried and concentrated to furnish a solid. Recrystallization from CHCl$_3$/hexane gave 1.2 g of N-(4-chlorophenyl)-4-methoxy-2,2-dimethyl-3-butenamide (Compound 42), m.p. 93° C.

EXAMPLE 18

3-Fluoro-2,2-dimethylbutenoic acid

Lithium diisopropyl amide (0.142 mole) was prepared by adding n-butyllithium (65 mL of 2.2M, 0.142 mole) to a stirred solution of diisopropyl amine (14.3 g, 0.142 mole) in 200 mL of dry tetrahydrofuran at $-50°$ C. Ethyl isobutyrate (14.9 g, 0.129 mole) was then added dropwise to the stirred cold solution. The solution was stirred an additional 1 hour at $-60°$ C., then hexamethylphosphoramide (HMPA: 23.1 g, 0.129 mole) was added in one portion.

In a separate flask 1,2-dibromo-1,1-difluoroethane (32 g, 0.142 mole) was added dropwise to a stirred slurry of powdered zinc (16.9 g, 0.258 g at.) in 75 mL of absolute ethanol. The resulting gaseous 1,1-difluoroethylene was bubbled through the cold anionic solution. After the addition was complete, the reaction mixture was allowed to warm to room temperature with stirring over the next two hours. The solution was then poured onto a solution containing 200 g of crushed ice and 25 mL of concentrated hydrochloric acid, and the product was extracted into 2×200 ml of ether. The combined organic layer was then washed with 2×200 mL of water and dried over anhydrous magnesium sulfate. Concentration under vacuum at 0° C. yielded 19 g of a yellow oil. Distillation yielded 12.0 g of ethyl 3-fluoro-2,2-dimethyl-3-butenoate as a clear colorless oil boiling at 30°-55° C. at 25 mm Hg.

Hydrolysis of the ester (1 g) with 1 g of potassium hydroxide in ethanol/water overnight furnished 0.65 g of the title acid.

EXAMPLE 19

N-(4-chlorophenyl)-3-fluoro-2,2-dimethyl-3-butenamide (Compound 43)

3-Fluoro-2,2-dimethylbut-3-enoic acid (1 g) was converted to 0.17 g of N-(4-chlorophenyl)-3-fluoro-2,2-dimethyl-3-butenamide, m.p. 75°-76° C., according to the procedure described in Example 2.

EXAMPLE 20

(Z)-4-Bromo-3-fluoro-2,2-dimethyl-3-butenoic acid

Ethyl 3-fluoro-2,2-dimethyl-3-butenoate (14 g) and bromine (11 g) were dissolved in 50 mL of $CCl_4$, and the solution heated at reflux for one hour. The solution was then cooled and concentrated in vacuo. The dibromo ester was taken up in 100 mL of dry THF and stirred at 0° C. while DBU (13 g) was added dropwise. Stirring was continued overnight, allowing the solution to warm to ambient temperature. The dark solution was then poured onto ice and excess 10N HCl, and the product was isolated by extraction into ether, washing with a saturated brine solution, drying and removal of the solvent. The bromovinyl ester (10.4 g) was then hydrolyzed by treatment with 7.3 g of potassium hydroxide in a solution of 10 mL of ethanol and 90 mL of water, at the reflux temperature for one hour. After the solution had cooled, it was diluted with 100 mL of water, acidified, extracted with ether (2×100 mL), and the combined organic layer washed with brine, dried and concentrated to yield 7.3 g of (Z) 4-bromo-3-fluoro-2,2-dimethyl-3-butenoic acid as an oil.

EXAMPLE 21

(Z)-4-Bromo-N-(4-chlorophenyl)-3-fluoro-2,2-dimethyl-3-butenamide (Compound 44)

4-Bromo-3-fluoro-2,2-dimethyl-3-butenoic acid (1 g) was converted to the corresponding p-chloroanilide according to the procedure described in Example 2 to furnish 1.06 g of the title compound as a solid, m.p. 131°-133° C.

EXAMPLE 22

(Z)-4-Chloro-3-fluoro-2,2-dimethylbut-3-enoic acid

Ethyl 3-fluoro-2,2-dimethyl-3-butenoate (7.75 g) in 100 mL of $CCl_4$ was stirred and treated with gaseous chlorine (excess), resulting in a temperature increase to 50° C. The solution was allowed to stir at ambient temperature an additional 16 hours, then partitioned between ether and water. The organic layer was dried over $MgSO_4$, filtered and concentrated to give 10.1 g of the dichloride as a clear yellow oil. This was taken up in 20 mL of DMF and added dropwise to a stirred, cooled (0° C.) suspension of potassium t-butoxide (8.3 g) in 100 mL of DMF. Stirring was continued overnight, allowing the solution to warm to ambient temperature. The dark solution was then poured onto ice and extracted twice with ether. The combined organic layer was washed with brine, dried and concentrated to yield 4.8 g of ethyl 4-chloro-3-fluoro-2,2-dimethylbut-3-enoate as a red oil. Hydrolysis with 3 g of potassium hydroxide in ethanol/water as described in Example 4 yielded 3 g of (Z)-4-chloro-3-fluoro-2,2-dimethylbut-3-enoic acid as an oil.

EXAMPLE 23

(Z)-N-(4-Bromophenyl)-4-fluoro-2,2-dimethyl-3-butenamide (Compound 46)

4-Chloro-3-fluoro-2,2-dimethylbut-3-enoic acid (1 g) was converted to the title compound (m.p. 118°-121° C.) using the procedure described in Example 2. Yield 0.62 g.

EXAMPLE 24

4,4-Dibromo-N-(4-chlorophenyl)-2,2-dimethyl-3-butenamide (Compound 47)

Using the procedure described by Corey and Fuchs, *Tetrahedron Letters*, p 3769, 1972, N-(chlorophenyl)-2,2-dimethyl-3-oxopropanamide (1 g), which was prepared as described in Example 9, and carbon tetrabromide (3 g) were dissolved in 75 mL of dichloromethane, the solution was cooled, and triphenylphosphine (4.6 g) in 20 mL of dichloromethane was added dropwise over 30 minutes. After the solution was stirred one hour, an additional 1 g of triphenylphosphine was added. Ether (100 mL) was then added, and the solution was filtered through a silica gel column to remove triphenylphosphine oxide (eluting with ether). The filtrate fractions which contained the product were concentrated to give the title compound, a solid, m.p. 104° C.

EXAMPLE 25

4-Fluoro-2,2-dimethylbut-3-enoic acid

Using the procedure for iodofluorination of olefins described by L. D. Hall and D. L. Jones in *Can. J. Chem.*, Vol. 51 (1973), p 2902, ethyl 2,2-dimethylbut-3-enoate (2.5 g) and silver fluoride (6.7 g) were stirred vigorously in 50 mL of benzene cooled to 5° C. while iodine (4.7 g) in 80 mL of benzene was added dropwise. After addition was complete, 30 mL of acetonitrile was added and the solution was allowed to warm to ambient temperature and stirred overnight. The solution was then filtered and the filtrate washed with a saturated bicarbonate solution, then with a saturated sodium thiosulfate solution. Drying and concentration furnished 3.1 g of an oil, which was taken up immediately in 30 mL of DMF and treated portionwise with 1.3 g of potassium t-butoxide, with stirring at −5° C. After the addition was complete, the solution was allowed to warm to ambient temperature over 2 hours, then diluted with 100 mL of ether and washed with cold water. Drying and concentration furnished 1.25 g of (Z) Ethyl 4-fluoro-2,2-dimethylbut-3-enoate as an oil.

The ester was hydrolyzed to the acid with 2 g of potassium hydroxide in 20 ml of ethanol and 10 mL of water, according to the procedure described above, to furnish 0.4 g of the title compound.

EXAMPLE 26

(E)-N-(4-bromophenyl)-4-fluoro-2,2-dimethyl-3-butenamide (Compound 48)

The 4-Fluoro-2,2-dimethylbut-3-enoic acid produced in Example 25 was converted to the title compound, (0.22 g after recrystallization from ether/petroleum ether, m.p. 87°–90° C.), by the procedure described in Example 2.

EXAMPLE 27

4,4-Dichloro-N-(4-chlorophenyl)-2,2-dimethyl-3-butenamide (Compound 49)

4,4-Dichloro-2,2-dimethylbut-3-enoic acid (0.45 g) was then converted to the corresponding p-chloroanilide according to the conditions described in Example 2, which after recrystallization gave 0.45 g of 4,4-Dichloro-N-(4-chlorophenyl)-2,2-dimethyl-3-butenamide (m.p. 131°–134° C.) free of mono-chloro impurity.

The compounds of the present invention are useful both as preemergent and postemergent herbicides. Therefore, yet another embodiment of the invention is a method of controlling undesired plants which comprises applying the plants, or to the locus of the plants, a growth inhibiting amount of a compound of formula (1).

The compounds of the present invention display activity against a wide variety of weeds. Examples of typical weeds include, but are not limited to, the following:

Wild Oat (*Avena fatua*)
Catchweed Bedstraw (*Galium aparine*)
Scentless Mayweed (*Matricaria incdora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (Chrysanthemum spp.)
Common Purslane (*Portulaca oleracea*)
Sida (Sida spp.)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarters (*Chenopodium album*)
Green Smartweed (*Polygonum scabrum*)
Green Foxtail (*Setaria viridis*)
Redroot Pigweed (*Amaranthus retroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium rigidum*)
Kapeweed (*Cryptostemma calendula*)
Purple Loosestrife (*Lythrum salicaria*)
Wild radish (*Raphanus raphanistrum*)
Wireweed (*Polygonum aviculare*)
Henbit (*Laminum amplexicaule*)
Wild Mustard (*Brassica kaber*)
Barnyardgrass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sanbur (*Cenchrus echinatus*)
Large Crabgrass (*Digitaria sanguinalis*)
Cheat (*Bromus secalinus*)
Morningglory (Ipomea spp.)
Common Ragweed (*Ambrosia artemisiifolia*)
Common Milkweed (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Large Crabgrass (*Digitaria sanguinalis*)
Prickly Sida (*Sida spinosa*)
Corn Gromwell (*Lithospermum arvenase*)
Yellow Foxtail (*Setaria glauca*)
Tansymustard (*Descurainia pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmondium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiforum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoea hederacea*)
Fall Panicum (*Panicum dichotomiflorum*)
Powell Amaranth (*Amaranthus powellii*)
Texas Panicum (*Panicum texanum*)
Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegens*)
Nightshade (Solanum spp.)

The term "growth inhibiting amount", as defined herein, refers to an amount of a compound of the invention which either kills or stunts the growth of the weed species for which control is desired. This amount will generally be from about 0.05 to about 20.0 pounds or greater of a compound of the invention per acre (about 0.056 to about 22.4 kg/ha). The compounds are more preferably applied at rates of about 0.10 to about 8.0 lb/A (about 0.112 to about 8.96 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with a compound of the invention. These compounds can be applied to the soil to selectively control undesired plants by soil contact when the weed seeds are germinating and emerging. They can also be used directly to kill emerged weeds by direct contact with the exposed portion of the weed.

The compounds of the present invention are preferably formulated with a suitable agriculturally-acceptable carrier for ease of application. Such compositions will contain from about 0.1 to about 95.0 percent by weight of the active ingredient, depending on the composition desired. Examples of typical herbicidal compositions contemplated as another aspect of the present invention include sprayable formulations, such as wettable powders, aqueous suspensions and emulsifiable concentrates; and solid compositions, such as dusts and granules.

The most convenient formulations are in the form of concentrated compositions to be applied by spraying as water dispersions or emulsions containing in the range from about 0.1 percent to about 10 percent of the active agent by weight. Water-dispersible or emulsifiable compositions may be either solids, usually known as wettable powders, or liquids, usually known as emulsifiable concentrates and aqueous suspensions.

A typical wettable powder comprises an intimate mixture of an active ingredient of the invention, an inert carrier, and one or more surfactants. The concentration of the active agent is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed naphthalenesulfonates, and the alkyl sulfates.

A typical emulsifiable concentrate comprises from about 0.1 to about 6 pounds of a compound of the invention per gallon of liquid (about 0.0112 to about 0.672 kg/l), dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents, as well as water and the active ingredient.

Dust compositions containing a compound of the present invention usually contain from about 0.1 to about 10 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particle size. The active ingredient is most conveniently applied to the clay by dissolving it in an inexpensive solvent, such as acetone, and applying the solution to the sized clay in an appropriate solids mixer. The solvent is then typically removed by evaporation prior to applying the granules to the application site.

When operating in accordance with the present invention, the present compounds or compositions thereof, may be applied to the site where herbicidal or algicidal control is desired by any convenient manner, e.g., by means of hand dusters or sprayers. Metering applicators can apply accurately measured quantities of granular compositions to the locus to be treated. Other applications can be carried out with power dusters, boom sprayers, high-pressure sprayers and spray dusters. In large scale operations, dusts or low-volume sprays can be applied aerially, for example from airplanes or helicopters, to the application site. When applying the formulations described above, it is important to apply the desired concentrations of active ingredient uniformly to the plants or locus to be treated.

The following examples provide illustrations of typical agriculturally-acceptable compositions comprehended by this invention.

| Ingredient | Concentration Weight Percent |
|---|---|
| Aqueous Suspension | |
| Compound 7 | 12.2 |
| TERGITOL TMN-6 (nonionic surfactant) | 5.0 |
| ZEOSYL-200 (silica) | 1.0 |
| POLYFON H (anionic lignosulfonate wetting agent) | 0.5 |
| 2% xanthan solution (thickening agent) | 10.0 |
| ANTIFOAM AF-100 (silicon based antifoam agent) | 0.2 |
| tap water | 71.0 |
| Emulsifiable Concentrate | |
| Compound 11 | 13.0 |
| SPONTO 1003 (anionic/nonionic surfactant blend) | 12.0 |
| DMF | 6.0 |
| DOWANOL PM (propylene glycol monomethyl ether) | 12.0 |
| EXXON-200 (naphthalenic solvent) | 57.0 |
| Compound 15 | 13.0 |
| SPONTO 1003 | 12.0 |
| DMF | 6.0 |
| DOWANOL PM | 12.0 |
| EXXON-200 | 57.0 |
| Compound 19 | 6.2 |
| TOXIMUL H/D blend (90/10) (a nonionic/anionic surfactant blend) | 6.0 |
| N-methylpyrrolidone | 7.0 |
| EXXON-200 | 80.8 |
| Compound 19 | 12.37 |
| TOXIMUL H/D blend (90/10) | 5.00 |
| N-methylpyrrolidone | 12.00 |
| EXXON-200 | 70.63 |
| Compound 26 | 12.5 |
| SPONTO 500T (an anionic/nonionic surfactant blend) | 10.0 |
| N-methylpyrrolidone | 12.0 |

| Ingredient | Concentration Weight Percent |
|---|---|
| EXXON-200 | 65.5 |

The herbicidal activity of representative compounds of the present invention is illustrated by the following experiments.

EXPERIMENT 1

The initial screen used to evaluate herbicidal efficacy, was conducted at a test compound concentration of 8 lb/A (9 kg/ha). In this test tomato, large crabgrass and pigweed seeds were planted by row in containers containing standard growing media.

The test compounds were formulated for application by dissolving the compound into a solvent prepared by combining TOXIMUL R and TOXIMUL S (proprietary blends of anionic and nonionic surfactants manufactured by Stepan Chemical Company, Northfield, Ill.) with a 9:1 (v/v) mixture of acetone:ethanol. The solvent/compound solution was diluted with deionized water and applied postemergence to some planted containers and preemergence to others using a compressed air sprayer at low pressure. Postemergence treatment was made 8 to 10 days after planting while preemergence treatment was made 1–2 days after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury, and "5" indicates death to the plant or no seedling emergence. A "0" indicates that no reading was taken. Also, the various types of injury of each test species were coded as follows:

| | |
|---|---|
| A = | abscission of leaves |
| B = | burned |
| C = | chlorosis |
| D = | death |
| E = | epinasty |
| F = | formation effects |
| G = | dark green |
| I = | increased plant growth |
| N = | no germination |
| P = | purple pigmentation |
| R = | reduced germination |
| S = | stunting |

Table I presents the herbicidal activity of typical compounds of the invention when evaluated in the screen described above.

TABLE I

| | Herbicide Screen at 8 lb/A (9 kg/ha) | | | | | |
|---|---|---|---|---|---|---|
| | Preemergence | | | Postemergence | | |
| Compound Number | Tomato | Crab-grass | Pig-weed | Tomato | Crab-grass | Pig-weed |
| 1 | 3BS | 2S | 0 | 1 | 1 | 1 |
| 2 | 1 | 1 | 1 | 1 | 1 | 1 |
| 3 | 4BS | 4BS | 4BS | 5D | 5D | 5D |
| 4 | 4BS | 3RS | 5D | 5D | 5D | 5D |
| 5 | 2SC | 4SC | 4BS | 5D | 4BS | 5D |
| 6 | 4SB | 4BS | 4RS | 5D | 5D | 5D |
| 7 | 1 | 1 | 1 | 1 | 1 | 1 |
| 19 | 4BS | 4BS | 4BS | 5D | 5D | 5D |
| 20 | 5D | 4BS | 5D | 5D | 5D | 5D |
| 21 | 5D | 2S | 5D | 5D | 3BS | 4B |
| 22 | 5D | 1 | 5D | 5D | 1 | 3B |
| 23 | 5D | 4BS | 5D | 5D | 5D | 5D |
| 24 | 4RS | 2RS | 5D | 0 | 1 | 0 |
| 25 | 4BS | 4RS | 5D | 5D | 5D | 5D |
| 26 | 4BS | 4BS | 5D | 5D | 5D | 5D |
| 27 | 5D | 4BS | 5D | 5D | 5D | 5D |
| 28 | 0 | 0 | 0 | 5D | 4BS | 4B |
| 29 | 2B | 1 | 2BS | 5D | 2BS | 3B |
| 32 | 2C | 2RS | 4RS | 1 | 1 | 1S |
| 33 | 2CS | 3RS | 4RS | 5D | 4BS | 5D |
| 34 | 1 | 1 | 1 | 1 | 1 | 1 |
| 36 | 1 | 2S | 1 | 1 | 1 | 1 |
| 37 | 1 | 3S | 2S | 1 | 1 | 1 |
| 38 | 1 | 3S | 2RS | 2SB | 1 | 2S |
| 39 | 1 | 3FS | 2FS | 1 | 1 | 1 |
| 40 | 2RS | 3FS | 2FS | 1 | 1 | 1 |
| 41 | 1 | 1 | 1 | 1 | 2FS | 1 |
| | 1 | 1 | 1 | 5D | 2BS | 2B |
| 42 | 1 | 3RS | 2RS | 5D | 3BS | 5D |
| | 1 | 1 | 1 | 1 | 1 | 1 |
| 44 | 2BS | 2S | 5D | 5D | 1 | 5D |
| 45 | 0 | 0 | 0 | 1 | 1 | 1 |
| 47 | 3SF | 2S | 4BS | 5D | 2BS | 5D |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above described formulations with a mixture of the surfactant containing solvent and deionized water. The compounds were evaluated according to the general procedure outlined above. Table II presents the postemergence herbicidal tests results, while Table III presents preemergence test data, both applications being administered at 4 lbs/A (4.5 kg/ha) or less.

The species employed in these tests are coded as follows in Tables II and III:

| | |
|---|---|
| A = | corn |
| B = | cotton |
| C = | soybean |
| D = | wheat |
| E = | barley |
| F = | sugarbeet |
| G = | rice |
| H = | tomato |
| I = | lambsquarter |
| J = | crabgrass |
| K = | mustard |
| L = | pigweed |
| M = | foxtail |
| N = | wild oat |
| O = | velvetleaf |
| P = | morningglory |

TABLE II

Postemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
| 1 | 8.000 | | | | | | | | 1 | | 1 | | 1 | | | | |
| | 4.000 | | | 3BS | | 2BS | | | 5D | | 3BS | 4BS | 5D | 4BS | | | 4BS |
| | 2.000 | 2BS | 4BS | 3B | 1 | 2B | 3BS | 2B | 4BS | 2BS | 2BS | 2BS | 4BS | 3BS | 1 | 1 | 0 |
| | 1.000 | 1 | 3BS | 2B | 1 | 2B | 3BS | 2B | 3BS | 2BS | 2BS | 3BS | 3BS | 2BS | 1 | 1 | 3BS |
| | 0.500 | 1 | 2B | 2B | 1 | 2B | 2BS | 1 | 2BS | 2BS | 1 | 2BS | 2BS | 2B | 1 | 1 | 2B |
| 2 | 4.000 | | | 3BS | | 2BS | | | 1 | | 3BS | 4BS | 5D | 5D | | | 5D |
| | 2.000 | 1 | 4BS | 2B | 1 | 1 | 4BS | 1 | 1 | 2BS | 3BS | 3BS | 4BS | 2BS | 1 | 2BS | 0 |
| | 1.000 | 1 | 3BS | 2B | 1 | 1 | 3BS | 1 | 1 | 2BS | 2BS | 2BS | 3BS | 2BS | 1 | 1 | 5D |
| | 0.500 | 1 | 2BS | 2B | 1 | 1 | 2BS | 1 | 1 | 1 | 2BS | 1 | 2BS | 1 | 1 | 1 | 3BS |
| 3 | 8.000 | | | | | | | | 5D | | 5D | | 5D | | | | |
| | 4.000 | | | 3BS | | 2BS | | | 5D | | 4BS | 5D | 5D | 5D | | 4BS | 4BS |
| | 2.000 | 3BS | 4BS | 4BS | 1 | 2B | 4BS | 2B | 5D | 4BS | 5D | 5D | 5D | 4BS | 2BS | 4BS | 3BS |
| | 1.000 | 1 | 4BS | 3B | 1 | 2B | 4BS | 2B | 5D | 4BS | 4BS | 4BS | 5D | 3BS | 1 | 3BS | 3BS |
| | 0.500 | 1 | 3BS | 3B | 1 | 1 | 3BS | 1 | 3BS | 2BS | 3BS | 3BS | 4BS | 3BS | 1 | 2S | 3BS |
| 4 | 8.000 | | | | | | | | 5D | | 5D | | 5D | | | | |
| | 4.000 | | | 4BS | | 3BS | | | 5D | | 5D | 5D | 5D | 5D | | | 4BS |
| | 2.000 | 2BS | 4BS | 5D | 4BS | 4BS | 5D | 3BS | 5D | 5D | 5D | 5D | 5D | 5D | 4BS | 5D | 5D |
| | 0.500 | 1 | 4BS | 3BS | 2BS | 2BS | 3BS | 2BS | 5D | 4BS | 5D | 5D | 5D | 4BS | 3BS | 4BS | 3BS |
| 5 | 8.000 | | | 2BS | | 2B | | | 5D | | 4BS | | 5D | | | | 3BS |
| | 4.000 | | | 2BS | | 2B | | | 5D | | 3BS | 5D | 5D | 2BS | | | 3BS |
| | 2.000 | 1 | 3BS | 2BS | 1 | 1 | 3BS | 1 | 4BS | 3BS | 5D | 4BS | 5D | 1 | 1 | 4BS | 3BS |
| | 1.000 | 1 | 2BS | 2BS | 1 | 1 | 2BS | 1 | 3BS | 2BS | 3BS | 3BS | 3BS | 1 | 1 | 2BS | 2BS |
| | 0.500 | 1 | 1 | 1 | 1 | 1 | 2BS | 1 | 2BS | 1 | 1 | 2BS | 2BS | 1 | 1 | 2BS | 2BS |
| 6 | 8.000 | | | | | | | | 5D | | 5D | | 5D | | | | |
| | 4.000 | | | 4BS | | 4BS | | | 5D | | 5D | 4BS | 5D | 5D | | | 3BS |
| | 2.000 | 2BS | 4BS | 0 | 3BS | 3BS | 5D | 2BS | 5D | 5D | 5D | 5D | 5D | 5D | 3BS | 4BS | 4BS |
| | 1.000 | 2B | 3BS | 0 | 2BS | 2BS | 4BS | 2BS | 5D | 5D | 5D | 5D | 5D | 5D | 3BS | 3BS | 4BS |
| | 0.500 | 2BS | 3BS | 0 | 2BS | 2BS | 4BS | 2B | 4BS | 3BS | 4BS | 4BS | 5D | 4BS | 2BS | 3BS | 3BS |
| 7 | 4.000 | | | 4BS | | 4BS | | | 5D | | 5D | 4BS | 5D | 0 | | | 5D |
| | | | | 3BS | | 4BS | | | 5D | | 5D | 5D | 5D | 5D | | | 4BS |
| | 2.000 | 3BS | 5D | 5D | 3BS | 3BS | 5D | 0 | 5D | 5D | 5D | 5D | 5D | 5D | 4BS | 5D | 4BS |
| | 1.000 | 3BS | 5D | 4BS | 2BS | 2BS | 5D | 0 | 5D | 5D | 5D | 5D | 5D | 5D | 4BS | 5D | 3BS |
| | 0.500 | 2BS | 4BS | 2BS | 1 | 2BS | 3BS | 0 | 5D | 4BS | 5D | 5D | 5D | 5D | 2BS | 4BS | 3BS |
| 8 | 4.000 | | | 2BS | | 3BS | | | 5D | | 5D | 5D | 5D | 0 | | | 4BS |
| | 2.000 | 4BS | 5D | 5D | 4B | 4BS | 5D | 0 | 5D | 4BS | 5D | 5D | 5D | 5D | 4BS | 5D | 4BS |
| | 1.000 | 3BS | 5D | 3BS | 3BS | 3BS | 5D | 0 | 5D | 4BS | 5D | 5D | 5D | 5D | 4BS | 0 | 4BS |
| | 0.500 | 2BS | 3BS | 2BCS | 2BS | 2BS | 4BS | 0 | 5D | 2BS | 5D | 4BS | 4BS | 4BS | 3BS | 5D | 3BS |
| 9 | 4.000 | | | 3BS | | 2BS | | | 3BS | | 4BS | 4BS | 5D | 3BS | | | 4BS |
| | 2.000 | 3BS | 4BS | 4BS | 2S | 2BS | 4BS | 3BS | 5D | 3BS | 4BS | 4BS | 5D | 5D | 2B | 3BS | 3BS |
| | 1.000 | 2S | 3BS | 3BS | 1 | 2B | 3BS | 2BS | 5D | 3BS | 3BS | 3BS | 4BS | 4BS | 2B | 2B | 2B |
| | 0.500 | 2S | 2BS | 2BS | 1 | 1 | 1 | 1 | 3BS | 1 | 2B | 2BS | 2BS | 2BS | 1 | 1 | 2B |
| 10 | 4.000 | | | 4BS | | 2BS | | | 4BS | | 5D | 5D | 5D | 5D | | | 4BS |
| | 2.000 | 2BS | 4BS | 3BS | 2BS | 2BS | 4BS | 3BS | 2BS | 4BS | 4BS | 4BS | 4BS | 4BS | 2BS | 3BS | 1 |
| | 1.000 | 1 | 3BS | 2BS | 1 | 1 | 3BS | 2BS | 2BS | 4BS | 3BS | 3BS | 4BS | 3BS | 1 | 3BS | 1 |
| | 0.500 | 1 | 2S | 2B | 1 | 1 | 2BS | 1 | 2BS | 3BS | 3BS | 3BS | 4BS | 3BS | 1 | 1 | 1 |
| 11 | 4.000 | | | 4BS | | 3BS | | | 5D | | 5D | 5D | 5D | 5D | | | 5D |
| | 2.000 | 3BS | 5D | 5D | 4BS | 4BS | 5D | 3BS | 5D | 4BS | 5D | 5D | 5D | 5D | 4BS | 4BS | 5D |
| | 1.000 | 3BS | 5D | 5D | 3BS | 3BS | 4BS | 2BS | 5D | 4BS | 4BS | 5D | 5D | 5D | 3BS | 4BS | 5D |
| | 0.500 | 2BS | 4BS | 3BS | 3BS | 2BS | 3BS | 2BS | 5D | 4BS | 4BS | 5D | 5D | 4BS | 3BS | 5D | 4BS |
| 12 | 4.000 | | | 4BS | | 3BS | | | 5D | | 5D | 5D | 5D | 5D | | | 5D |
| | 2.000 | 2BS | 5D | 4BS | 2BS | 3BS | 5D | 3BS | 4BS | 4BS | 5D | 5D | 5D | 4BS | 4BS | 4BS | 4BS |
| | 1.000 | 2BS | 4BS | 3BS | 2BS | 2BS | 4BS | 2BS | 4BS | 4BS | 4BS | 5D | 5D | 4BS | 3BS | 3BS | 4BS |
| | 0.500 | 2BS | 3BS | 3BS | 2BS | 2BS | 4BS | 2BS | 3BS | 3BS | 4BS | 5D | 5D | 3BS | 2B | 2BS | 3BS |
| 13 | 4.000 | | | 1 | | 1 | | | 3BS | | 2BS | 3BS | 2BS | 2BS | | | 2BS |
| 14 | 4.000 | | | 3BS | | 3BS | | | 5D | | 5D | 5D | 5D | 4BS | | | 5D |
| | 2.000 | 2BS | 5D | 3BS | 3BS | 3BS | 5D | 3BS | 5D | 2BS | 5D | 5D | 5D | 4BS | 5D | 4BS | 4BS |
| | 1.000 | 1 | 5D | 3BS | 2BS | 3BS | 5D | 2BS | 5D | 1 | 4BS | 5D | 2BS | 4BS | 3BS | 4BS | 4BS |
| | 0.500 | 1 | 4BS | 2B | 2B | 2BS | 4BS | 2B | 5D | 1 | 3BS | 4BS | 3BS | 3BS | 2BS | 3BS | 4BS |
| 15 | 4.000 | | | 5D | | 5D | | | 5D | | 5D | 5D | 5D | 5D | | | 5D |
| | | | | 5D | | 5D | | | 5D | | 5D | 5D | 5D | 5D | | | 5D |
| | 2.000 | 5D | 5D | 5D | 4BS | 4BS | 5D | 4BS | 5D | 5D | 5D | 5D | 5D | 5D | 5D | 5D | 5D |
| | 1.000 | 4BS | 5D | 4BS | 3BS | 4BS | 5D | 3BS | 5D | 5D | 4BS | 5D | 5D | 5D | 5D | 5D | 5D |
| | 0.500 | 2BS | 5D | 4BS | 3BS | 3BS | 5D | 3BS | 5D | 4BS | 3BS | 4BS | 5D | 5D | 5D | 4BS | 5D |
| 16 | 4.000 | | | 4BS | | 4BS | | | 5D | | 5D | 5D | 5D | 5D | | | 5D |
| | 2.000 | 2BS | 5D | 3BS | 3BS | 3BS | 5D | 3BS | 5D | 5D | 5D | 5D | 5D | 5D | 5D | 5S | 4BS |
| | 1.000 | 2BS | 5D | 3BS | 3BS | 3BS | 5D | 3BS | 5D | 4BS | 4BS | 4BS | 5D | 5D | 4BS | 5D | 3BS |
| | 0.500 | 1 | 4BS | 3BS | 1 | 2B | 5D | 2B | 5D | 3BS | 3BS | 4BS | 5D | 5D | 2BS | 4BS | 2BS |
| 17 | 4.000 | | | 3BS | | 1 | | | 4BS | | 3BS | 4BS | 5D | 5D | | | 4BS |
| | 2.000 | 1 | 2BS | 3BS | 1 | 1 | 5D | 1 | 4BS | 0 | 5D | 3BS | 5D | 5D | 1 | 5D | 5D |
| | 1.000 | 1 | 4BS | 3BS | 1 | 1 | 5D | 2B | 2BS | 1 | 3BS | 2BS | 3BS | 5D | 1 | 3BS | 4BS |
| | 0.500 | 1 | 3BS | 2B | 1 | 1 | 5D | 1 | 2BS | 0 | 2BS | 2BS | 0 | 2BS | 1 | 2BS | 4BS |
| 18 | 4.000 | | | 5D | | 4BS | | | 5D | | 5D | 5D | 5D | 5D | | | 5D |
| | 2.000 | 4BS | 5D | 5D | 4BS | 4BS | 5D | 4BS | 5D | 5D | 5D | 5D | 5D | 5D | 5D | 5D | 5D |
| | 1.000 | 3BS | 5D | 3BS | 3BS | 3BS | 5D | 3BS | 5D | 5D | 5D | 5D | 5D | 5D | 4BS | 5D | 4BS |
| | 0.500 | 2BS | 5D | 3BS | 3BS | 3BS | 5D | 3BS | 5D | 5D | 5D | 5D | 5D | 5D | 4BS | 5D | 4BS |
| | | 2BS | 5D | 2BS | 3BS | 3BS | 4BS | 3BS | 5D | 5D | 4BS | 5D | 5D | 3BS | 5D | 2BS |
| | 0.250 | 2BS | 4BS | 3BS | 2BS | 2BS | 4BS | 3BS | 5D | 4BS | 4BS | 5D | 5D | 2BS | 4BS | 1 |
| | 0.125 | 2BS | 3BS | 2B | 1 | 1 | 3BS | 2BS | 2BS | 4BS | 2BS | 4BS | 5D | 4BS | 1 | 3BS | 1 |
| 19 | 8.000 | | | | | | | | 5D | | 5D | | 5D | | | | |

TABLE II-continued

Postemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
|  | 4.000 |  |  | 5D |  | 4BS |  |  | 5D |  | 5D | 5D | 5D | 5D |  |  | 5D |
|  |  |  |  | 5D |  | 4BS |  |  | 5D |  | 5D | 5D | 5D | 5D |  |  | 5D |
|  | 2.000 | 5D | 5D | 5D | 4BS | 5D | 5D | 4BS | 5D | 5D | 5D | 5D | 5D | 5D | 5D | 5D | 5D |
|  | 1.000 | 5D | 5D | 4BS | 4BS | 5D | 5D | 3BS | 5D | 5D | 5D | 5D | 5D | 5D | 5D | 5D | 5D |
|  | 0.500 | 2S | 4BS | 4BS | 3BS | 3BS | 4BS | 3BS | 5D | 5D | 4BS | 5D | 5D | 5D | 4BS | 4BS | 0 |
| 20 | 8.000 |  |  |  |  |  |  |  | 5D |  | 5D | 5D |  |  |  |  |  |
|  | 4.000 |  |  | 4BS |  | 5D |  |  | 5D |  | 5D | 5D | 5D | 5D |  |  | 5D |
|  | 2.000 | 3BS | 5D | 5D | 4BS | 4BS | 5D | 4BS | 5D | 5D | 4BS | 5D | 5D | 5D | 5D | 5D | 5D |
|  | 1.000 | 3BS | 5D | 2BS | 3BS | 4BS | 5D | 3BS | 5D | 5D | 3BS | 5D | 5D | 5D | 5D | 5D | 5D |
|  | 0.500 | 2B | 3BS | 2B | 2BS | 2BS | 3BS | 2BS | 5D | 4BS | 2BS | 5D | 4BS | 4BS | 3BS | 5D | 5D |
|  |  | 2BS | 5D | 3BS | 3BS | 3BS | 5D | 3BS | 5D | 5D | 2BS | 5D | 5D | 3BS | 3BS | 4BS | 3BS |
|  | 0.250 | 2BS | 4BS | 2BS | 2BS | 2BS | 3BS | 2BS | 3BS | 2BS | 1 | 4BS | 4BS | 3BS | 2BS | 4BS | 3BS |
|  | 0.125 | 2BS | 2BS | 2B | 2B | 2B | 3BS | 1 | 2BS | 1 | 1 | 3BS | 3BS | 1 | 1 | 3BS | 1 |
| 21 | 8.000 |  |  |  |  |  |  |  | 5D |  | 3BS |  | 4BS |  |  |  |  |
|  | 4.000 |  |  | 4BS |  | 4BS |  |  | 5D |  | 2BS | 5D | 4BS | 5D |  |  | 5D |
|  | 2.000 | 3BS | 5D | 4BS | 4BS | 5D | 3BS | 5D | 5D | 1 | 5D | 4BS | 5D | 5D | 5D | 5D |  |
|  | 1.000 | 3BS | 4BS | 3BS | 3BS | 3BS | 5D | 3BS | 5D | 2BS | 1 | 5D | 4BS | 5D | 3BS | 5D | 4BS |
|  | 0.500 | 2BS | 3BS | 2BS | 2BS | 2BS | 3BS | 2BS | 5D | 2BS | 1 | 5D | 2BS | 5D | 2BS | 5D | 3BS |
|  |  | 3BS | 4BS | 3BS | 3BS | 3BS | 3BS | 3BS | 5D | 2BS | 1 | 4BS | 2BS | 3BS | 2BS | 4BS | 3BS |
|  | 0.250 | 2BS | 2BS | 2BS | 2BS | 2BS | 3BS | 2BS | 4BS | 2BS | 1 | 4BS | 3BS | 3BS | 2BS | 3BS | 3BS |
|  | 0.125 | 2BS | 1 | 2B | 2B | 2B | 2BS | 1 | 2BS | 1 | 1 | 3BS | 2BS | 1 | 1 | 1 | 2B |
| 22 | 8.000 |  |  |  |  |  |  |  | 5D |  | 1 |  | 3BS |  |  |  |  |
|  | 4.000 |  |  | 2B |  | 2B |  |  | 4BS |  | 1 | 5D | 4BS | 3BS |  |  | 3BS |
|  | 2.000 | 2BS | 4BS | 2BS | 2BS | 2BS | 4BS | 2BS | 4BS | 1 | 2BS | 4BS | 4BS | 2BS | 1 | 2BS | 2BS |
|  | 1.000 | 2BS | 4BS | 2BS | 1 | 1 | 4BS | 1 | 3BS | 1 | 1 | 4BS | 4BS | 2BS | 1 | 2BS | 0 |
|  | 0.500 | 2 | 4BS | 2B | 1 | 1 | 3BS | 1 | 2BS | 1 | 1 | 3BS | 3BS | 3BS | 1 | 1 | 2BS |
| 22 | 8.000 |  |  |  |  |  |  |  | 5D |  | 1 |  | 3BS |  |  |  |  |
|  | 4.000 |  |  | 2B |  | 2B |  |  | 4BS |  | 1 | 5D | 4BS | 3BS |  |  | 3BS |
|  | 2.000 | 2BS | 4BS | 2BS | 2BS | 2BS | 4BS | 2BS | 4BS | 1 | 2BS | 4BS | 4BS | 2BS | 1 | 2BS | 2BS |
|  | 1.000 | 2BS | 4BS | 2BS | 1 | 1 | 4BS | 1 | 3BS | 1 | 1 | 4BS | 4BS | 2BS | 1 | 2BS | 0 |
|  | 0.500 | 1 | 4BS | 2B | 1 | 1 | 3BS | 1 | 2BS | 1 | 1 | 3BS | 3BS | 3BS | 1 | 1 | 2BS |
| 23 | 8.000 |  |  |  |  |  |  |  | 5D |  | 5D | 5D |  |  |  |  |  |
|  | 4.000 |  |  | 5D |  | 4BS |  |  | 5D |  | 4BS | 5D | 5D | 5D |  |  | 5D |
|  | 2.000 | 3BS | 5D | 3BS | 3BS | 2BS | 4BS | 2BS | 5D | 4BS | 2BS | 5D | 5D | 4BS | 3BS | 4BS | 5D |
|  | 1.000 | 2BS | 4BS | 2B | 1 | 1 | 2BS | 2BS | 5D | 3BS | 1 | 4BS | 3BS | 4BS | 2BS | 3BS | 3BS |
|  | 0.500 | 1 | 4BS | 2B | 1 | 1 | 2BS | 2B | 5D | 2BS | 1 | 2BS | 2BS | 4BS | 1 | 2BS | 2BS |
| 24 | 8.000 |  |  |  |  |  |  |  | 0 |  | 1 |  | 0 |  |  |  |  |
|  | 4.000 |  |  | 2BS |  | 2BS |  |  | 4BS |  | 3BS | 5D | 5D | 4BS |  |  | 3BS |
|  | 2.000 | 2BS | 5D | 2BS | 3BS | 3BS | 3BS | 2BS | 3BS | 1 | 1 | 4BS | 2BS | 4BS | 3BS | 3BS | 0 |
|  | 1.000 | 2BS | 3BS | 2B | 2BS | 3BS | 3BS | 2BS | 4BS | 1 | 1 | 4BS | 1 | 3BS | 2BS | 2BS | 0 |
|  | 0.500 | 1 | 2BS | 1 | 1 | 1 | 1 | 1 | 2BS | 1 | 1 | 4BS | 1 | 3BS | 2B | 2BS | 5D |
| 25 | 8.000 |  |  |  |  |  |  |  | 5D |  | 5D |  | 5D |  |  |  |  |
|  | 4.000 |  |  | 4BS |  | 4BS |  |  | 5D |  | 5D | 5D | 5D | 5D |  |  | 5D |
|  | 2.000 | 3BS | 5D | 3BS | 3BS | 4BS | 0 | 3BS | 5D | 5D | 2BS | 5D | 5D | 4BS | 4BS | 5D | 4BS |
|  | 1.000 | 2BS | 4BS | 2BS | 2BS | 2BS | 0 | 3BS | 5D | 3BS | 3BS | 5D | 4BS | 4BS | 3BS | 4BS | 2BS |
|  | 0.500 | 2BS | 3BS | 2B | 2BS | 2BS | 3BS | 2BS | 4BS | 1 | 1 | 5D | 3BS | 3BS | 2BS | 4BS | 2BS |
| 26 | 8.000 |  |  |  |  |  |  |  | 5D |  | 5D |  | 5D |  |  |  |  |
|  | 4.000 |  |  | 5D |  | 4BS |  |  | 5D |  | 5D | 5D | 5D | 5D |  |  | 5D |
|  | 2.000 | 3BS | 5D | 4BS | 4BS | 4BS | 5D | 0 | 5D | 5D | 5D | 5D | 5D | 5D | 4BS | 5D | 5D |
|  | 1.000 | 3BS | 4BS | 3BS | 3BS | 3BS | 5D | 0 | 5D | 5D | 4BS | 5D | 5D | 5D | 4BS | 5D | 4BS |
|  | 0.500 | 2B | 3BS | 3B | 2BS | 3BS | 5D | 0 | 5D | 5D | 4BS | 5D | 4BS | 5D | 3BS | 4BS | 3BS |
| 27 | 8.000 |  |  |  |  |  |  |  | 5D |  | 5D |  | 5D |  |  |  |  |
|  | 4.000 |  |  | 5D |  | 5D |  |  | 5D |  | 5D | 5D | 5D | 5D |  |  | 5D |
|  | 2.000 | 4BS | 5D | 5D | 4BS | 4BS | 5D | 3BS | 5D | 5D | 5D | 5D | 5D | 5D | 5D | 5D | 5D |
|  | 1.000 | 3BS | 5D | 5D | 3BS | 4BS | 5D | 3BS | 5D | 5D | 4BS | 5D | 5D | 5D | 5D | 5D | 4BS |
|  | 0.500 | 2BS | 5D | 4BS | 3BS | 4BS | 5D | 3BS | 5D | 5D | 3BS | 5D | 5D | 4BS | 4BS | 4BS | 4BS |
|  |  | 3BS | 5D | 4BS | 4BS | 4BS | 4BS | 4BS | 5D | 4BS | 1 | 5D | 4BS | 5D | 5D | 5D | 5D |
|  | 0.250 | 2B | 5D | 3BS | 3BS | 3BS | 2BS | 3BS | 5D | 4BS | 1 | 4BS | 4BS | 4BS | 3BS | 3BS | 2BS |
|  | 0.125 | 2B | 5D | 2BS | 2BS | 2BS | 2BS | 2B | 5D | 1 | 1 | 2BS | 1 | 3BS | 2B | 3BS | 1 |
| 28 | 8.000 |  |  |  |  |  |  |  | 5D |  | 4BS |  | 4BS |  |  |  |  |
|  | 4.000 |  |  | 4BS |  | 4BS |  |  | 5D |  | 3BS | 5D | 5D | 5D |  |  | 4BS |
|  | 2.000 | 2BS | 5D | 3BS | 3BS | 3BS | 5D | 3BS | 5D | 5D | 3BS | 5D | 4BS | 4BS | 3BS | 5D | 2B |
|  | 1.000 | 2BS | 4BS | 2BS | 2BS | 2BS | 4BS | 2BS | 4BS | 4BS | 1 | 4BS | 2BS | 3BS | 2BS | 4BS | 2B |
|  | 0.500 | 1 | 2BS | 1 | 1 | 1 | 3BS | .1 | 2BS | 4BS | 1 | 3BS | 1 | 2BS | 1 | 3BS | 2B |
| 29 | 8.000 |  |  |  |  |  |  |  | 5D |  | 2BS |  | 3BS |  |  |  |  |
|  | 4.000 |  |  | 2B |  | 3BS |  |  | 5D |  | 4BS | 4BS | 2BS | 5D |  |  | 5D |
|  | 2.000 | 3BS | 4BS | 2B | 2BS | 2BS | 5D | 2BS | 4BS | 2BS | 3BS | 4BS | 1 | 3BS | 3BS | 2BS | 4BS |
|  | 1.000 | 2BS | 3BS | 1 | 1 | 1 | 5D | 2B | 2BS | 2BS | 2BS | 4BS | 1 | 3BS | 3BS | 1 | 4BS |
|  | 0.500 | 2B | 2BS | 1 | 1 | 1 | 3BS | 1 | 2BS | 2BS | 1 | 3BS | 1 | 2BS | 2BS | 1 | 0 |
| 30 | 4.000 |  |  | 3BS |  | 2B |  |  | 3BS |  | 4BS | 4BS | 5D | 4BS |  |  | 3BS |
|  | 2.000 | 2BS | 3BS | 2BS | 1 | 2B | 3BS | 1 | 4BS | 3BS | 4BS | 4BS | 4BS | 3BS | 1 | 3BS | 2BS |
|  | 1.000 | 2B | 2BS | 2B | 1 | 2B | 3BS | 1 | 2BS | 1 | 2 | 3BS | 2B | 2BS | 1 | 1 | 2BS |
|  | 0.500 | 2B | 2B | 2B | 1 | 1 | 2BS | 1 | 2B | 1 | 1 | 2BS | 1 | 1 | 1 | 1 | 1 |
| 31 | 4.000 |  |  | 1 |  | 1 |  |  | 2BS |  | 1 | 2BS | 3BS | 2BS |  |  | 1 |
| 32 | 8.000 |  |  |  |  |  |  |  | 1 |  | 1 | 1 |  |  |  |  |  |
|  | 4.000 |  |  | 2BF |  | 1 |  |  | 2BS |  | 4BS | 3BS | 4BS | 3BS |  |  | 1 |
|  | 2.000 | 0 | 0 | 0 | 0 | 0 | 0 | 0 | 0 | 0 | 0 | 0 | 0 | 0 | 0 | 0 | 0 |
|  | 1.000 | 1 | 1 | 1 | 1 | 1 | 1 | 1 | 1 | 2BS | 2BS | 2BS | 3BS | 1 | 1 | 1 | 1 |
|  | 0.500 | 1 | 1 | 1 | 1 | 1 | 1 | 1 | 1 | 1 | 1 | 1 | 2BS | 1 | 1 | 1 | 1 |

TABLE II-continued

Postemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
| 33 | 8.000 | | | | | | | | 5D | | 4BS | | 5D | | | | |
| | 4.000 | | | 3BS | | 2BS | | | 5D | | 5D | 5D | 4BS | 4BS | | | 2B |
| | 2.000 | 1 | 3BS | 3BS | 1 | 1 | 3BS | 1 | 3BS | 4BS | 4BS | 4BS | 4BS | 4BS | 1 | 3BS | 1 |
| | 1.000 | 1 | 2BS | 2B | 1 | 1 | 3BS | 1 | 2BS | 3BS | 3BS | 3BS | 4BS | 3BS | 1 | 2S | 1 |
| | 0.500 | 1 | 1 | 1 | 1 | 1 | 2B | 1 | 1 | 2BS | 2B | 2BS | 3BS | 2B | 1 | 1 | 1 |
| 34 | 4.000 | | | 3CBS | | 2B | | | 3CBS | | 3CBS | 3CBS | 4BS | 2CS | | | 2BS |
| 35 | 4.000 | | | 2B | | 1 | | | 4BS | | 1 | 4BS | 5D | 2BS | | | 2B |
| | 2.000 | 1 | 2B | 1 | 1 | 1 | 3BS | 1 | 2BS | 2BS | 1 | 2BS | 3BS | 1 | 1 | 1 | 1 |
| | 1.000 | 1 | 1 | 1 | 1 | 1 | 2BS | 1 | 2BS | 1 | 1 | 1 | 2BS | 1 | 1 | 1 | 1 |
| | 0.500 | 1 | 1 | 1 | 1 | 1 | 1 | 1 | 1 | 1 | 1 | 1 | 1 | 1 | 1 | 1 | 1 |
| 39 | 4.000 | | | 2B | | 1 | | | 2B | | 1 | 2BS | 2FS | 1 | | | 1 |
| 40 | 4.000 | | | 2BFS | | 2B | | | 2B | | 1 | 3BS | 2B | 1 | | | 1 |
| 41 | 8.000 | | | | | | | | 5D | | 2BS | | 2BS | | | | |
| | 4.000 | | | 1 | | 2BS | | | 5D | | 2BS | 4BS | 4BS | 4BS | | | 3BS |
| | 2.000 | 2BS | 2BS | 2B | 2B | 1 | 4BS | 2BS | 2BS | 2BS | 3BS | 3BS | 3BS | 3BS | 1 | 1 | 1 |
| | 1.000 | 1 | 2B | 1 | 1 | 1 | 3BS | 1 | 2BS | 2BS | 2BS | 2BS | 2BS | 2B | 1 | 1 | 1 |
| | 0.500 | 1 | 1 | 1 | 1 | 1 | 2BS | 1 | 1 | 2BS | 2BS | 2BS | 2BS | 2B | 1 | 1 | 1 |
| 42 | 8.000 | | | | | | | | 5D | | 3BS | | 5D | | | | |
| | 4.000 | | | 2B | | 1 | | | 3BS | | 2B | 3SBF | 3BS | 2B | | | 2B |
| 43 | 4.000 | | | 2BS | | 2B | | | 2B | | 2BS | 2BS | 1 | 3BS | | | 1 |
| 44 | 8.000 | | | | | | | | 5D | | 1 | | 5D | | | | |
| | 4.000 | | | 4BS | | 3BS | | | 5D | | 3BS | 4BS | 5D | 5D | | | 4BS |
| | 2.000 | 3BS | 4BS | 3BS | 3BS | 3BS | 4BS | 3BS | 4BS | 0 | 4BS | 4BS | 0 | 4BS | 4BS | 4BS | 4BS |
| | 1.000 | 2BS | 3BS | 2BS | 2B | 2BS | 3BS | 2BS | 2BS | 0 | 3BS | 3BS | 0 | 3BS | 3BS | 3BS | 3BS |
| | 0.500 | 1 | 2B | 2B | 1 | 2B | 3BS | 1 | 2BS | 0 | 2BS | 3BS | 0 | 2BS | 2BS | 2BS | 2BS |
| 45 | 8.000 | | | | | | | | 1 | | 1 | | 1 | | | | |
| | 4.000 | | | 3BS | | 3BS | | | 5D | | 2BS | 3BS | 3BS | 5D | | | 5D |
| | 2.000 | 2B | 4BS | 3BS | 3BS | 3BS | 5D | 3BS | 5D | 0 | 0 | 4BS | 0 | 4BS | 4BS | 4BS | 3BS |
| | 1.000 | 2B | 4BS | 2BS | 2BS | 3BS | 2BS | 2BS | 4BS | 0 | 0 | 4BS | 0 | 5D | 3BS | 4BS | 3BS |
| | 0.500 | 2B | 4BS | 2BS | 2BS | 2BS | 2BS | 2BS | 3BS | 0 | 0 | 3BS | 0 | 4BS | 2BS | 3BS | 3BS |
| 46 | 4.000 | | | 3BS | | 2B | | | 5D | | 4BS | 5D | 5D | 5D | | | 0 |
| | 2.000 | 2S | 5D | 2S | 2BS | 3BS | 2BS | 3BS | 4BS | 4BS | 2BS | 4BS | 4BS | 5D | 3BS | 4BS | 2BS |
| | 1.000 | 2S | 3BS | 1 | 2B | 2B | 1 | 3BS | 5D | 3BS | 1 | 3BS | 2BS | 4BS | 2BS | 3BS | 1 |
| | 0.500 | 1 | 2B | 1 | 1 | 1 | 1 | 2BS | 2BS | 1 | 1 | 3BS | 1 | 2BS | 1 | 1 | 1 |
| 47 | 8.000 | | | | | | | | 5D | | 2BS | | 5D | | | | |
| | 4.000 | | | 3BS | | 2B | | | 4BS | | 4BS | 3BS | 5D | 3BS | | | 3BS |
| | 2.000 | 2BS | 3BS | 3BS | 2B | 2B | 4BS | 2B | 5D | 5D | 3BS | 3BS | 4BS | 2BS | 3BS | 3BS | 4BS |
| | 1.000 | 2B | 3BS | 3BS | 2B | 2B | 4BS | 2B | 5D | 4BS | 2B | 3BS | 4BS | 2BS | 3BS | 3BS | 4BS |
| | 0.500 | 1 | 2BCS | 2CB | 1 | 2B | 3BS | 1 | 4BS | 2BS | 1 | 2BS | 2BS | 2B | 2BS | 3BS | 3BCS |
| 48 | 4.000 | | | 5BS | | 5BS | | | 5BS | | 2BS | 5D | 3BS | 4BS | | | 5D |
| | 2.000 | 2BS | 5D | 3BS | 3BS | 3BS | 5D | 0 | 4BS | 2BS | 2S | 5D | 2S | 4BS | 3BS | 5D | 3BS |
| | 1.000 | 2BS | 3BS | 2BS | 2BS | 1 | 3BS | 0 | 3BS | 1 | 1 | 3BS | 1 | 4BS | 3BS | 3BS | 2BS |
| | 0.500 | 1 | 2B | 2B | 1 | 1 | 3BS | 0 | 2BS | 1 | 1 | 2BS | 1 | 3BS | 2B | 2S | 1 |
| 49 | 4.000 | | | 2BS | | 2B | | | 4BS | | 2BS | 4BS | 4BS | 3BS | | | 3BS |
| | 2.000 | 2BS | 4BS | 3BS | 2B | 2BS | 4BS | 2BS | 5D | 5D | 4BS | 5D | 5D | 3BS | 2BS | 1 | 2BS |
| | 1.000 | 1 | 3BS | 2B | 1 | 2B | 4BS | 2B | 4BS | 4BS | 2BS | 5D | 4BS | 3BS | 2BS | 1 | 2BS |
| | 0.500 | 1 | 2B | 2B | 1 | 2B | 3BS | 1 | 3BS | 2BS | 2B | 4BS | 2BS | 2B | 2B | 1 | 2BS |

TABLE III

Preemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
| 1 | 8.000 | | | | | | | | 3BS | | 2S | | 0 | | | | |
| | 4.000 | | | 1 | | 1 | | | 2BS | | 3FD | 3BS | 4BS | 1 | | | 1 |
| 2 | 4.00 | | | 1 | | 1 | | | 1 | | 1 | 1 | 4BS | 1 | | | 1 |
| 3 | 8.00 | | | | | | | | 4BS | | 4BS | | 4BS | | | | |
| | 4.000 | | | 2BS | | 2BS | | | 5D | | 4BS | 4BS | 5D | 4BS | | | 5D |
| | 2.000 | 1 | 1 | 1 | 1 | 1 | 3BS | 1 | 1 | 3S | 2S | 4BS | 5D | 2BS | 1 | 3BS | 1 |
| | 1.000 | 1 | 1 | 1 | 1 | 1 | 3S | 1 | 1 | 2S | 1 | 3BS | 5D | 1 | 1 | 2S | 1 |
| | 0.500 | 1 | 1 | 1 | 1 | 1 | 2S | 1 | 1 | 1 | 1 | 1 | 4BS | 1 | 1 | 1 | 1 |
| 4 | 8.000 | | | | | | | | 4BS | | 3RS | | 5D | | | | |
| | 4.000 | | | 2BS | | 1 | | | 5D | | 5D | 5D | 5D | 4BS | | | 1 |
| | 2.000 | 1 | 1 | 1 | 1 | 1 | 4BS | 2B | 4BS | 5D | 4BS | 5D | 5D | 2BS | 2B | 5D | 1 |
| | 1.000 | 1 | 1 | 1 | 1 | 1 | 3BS | 2BS | 2S | 4BS | 3S | 5D | 5D | 1 | 1 | 3BS | 1 |
| | 0.500 | 1 | 1 | 1 | 1 | 1 | 1 | 1 | 1 | 1 | 1 | 1 | 1 | 1 | 1 | 1 | 1 |
| 5 | 8.000 | | | | | | | | 2SC | | 4SC | | 4BS | | | | |
| | 4.000 | | | 1 | | 1 | | | 3BS | | 3S | 4BS | 0 | 2S | | | 2S |
| 6 | 8.000 | | | | | | | | 4BS | | 4BS | | 4RS | | | | |
| | 4.000 | | | 2S | | 1 | | | 2S | | 5N | 4RS | 5D | 5N | | | 2S |
| | 2.000 | 1 | 1 | 1 | 1 | 1 | 5N | 1 | 1 | 0 | 3RS | 4BS | 4RS | 2RS | 1 | 3RS | 1 |
| | 1.000 | 1 | 1 | 1 | 1 | 1 | 4RS | 1 | 1 | O | 2BS | 2BS | 4RS | 1 | 1 | 2RS | 1 |
| | 0.500 | 1 | 1 | 1 | 1 | 1 | 3RS | 1 | 1 | 0 | 1 | 1 | 3RS | 1 | 1 | 1 | 1 |
| 7 | 4.000 | | | 1 | | 2S | | | 5D | | 5D | 5D | 5D | 5D | | | 3BS |
| | | | 2S | | | 2BS | | | 5D | | 4BS | 4BS | 5D | 5D | | | 2S |
| | 2.000 | 1 | 1 | 1 | 2RS | 2RS | 4RS | 0 | 5D | 5D | 4BS | 2BS | 5D | 4BS | 2BS | 5D | 1 |
| | 1.000 | 1 | 1 | 1 | 1 | 2RS | 4 | 0 | 3BS | 4RS | 4RS | 2BS | 5D | 2S | 1 | 0 | 1 |

TABLE III-continued

Preemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
| | 0.500 | 1 | 1 | 1 | 1 | 2RS | 3RS | 0 | 2RS | 4RS | 1 | 1 | 4RS | 1 | 1 | 1 | 1 |
| 8 | 4.000 | | 2S | | 1 | | | | 4BS | | 4BS | 4BS | 5D | 4BS | | | 3RS |
| | 2.000 | 1 | 1 | 1 | 2RS | 2RS | 4RS | 0 | 2S | 4BS | 3RS | 1 | 4RS | 2S | 1 | 1 | 2RS |
| | 1.000 | 1 | 1 | 1 | 1 | 1 | 3RS | 0 | 1 | 3RS | 3RS | 1 | 3RS | 1 | 1 | 1 | 1 |
| | 0.500 | 1 | 1 | 1 | 1 | 1 | 2RS | 0 | 1 | 1 | 2S | 1 | 2RS | 1 | 1 | 1 | 1 |
| 9 | 4.000 | | | 1 | | 1 | | | 1 | | 2BS | 3BS | 0 | 3BS | | | 1 |
| 10 | 4.000 | | | 1 | | 1 | | | 1 | | 3BS | 2BS | 0 | 3BS | | | 0 |
| 11 | 4.000 | | | 2RS | | 2S | | | 3BS | | 5D | 4BS | 5D | 4BS | | | 0 |
| | 2.000 | 1 | 1 | 1 | 1 | 1 | 4RS | 1 | 5D | 5D | 5D | 5D | 5D | 4BS | 3BS | 5D | 1 |
| | 1.000 | 1 | 1 | 1 | 1 | 1 | 5N | 1 | 2BS | 4BS | 4BS | 5D | 5D | 1 | 1 | 4BS | 1 |
| | 0.500 | 1 | 1 | 1 | 1 | 1 | 4RS | 1 | 1 | 2BS | 1 | 4BS | 5D | 1 | 1 | 1 | 1 |
| 12 | 4.000 | | | 1 | | 2RS | | | 4BS | | 4BS | 4BS | 5D | 5D | | | 0 |
| | 2.000 | 1 | 3BS | 1 | 1 | 2B | 4BS | 1 | 5D | 4BS | 4BS | 5D | 4BS | 2BS | 5D | 2BS | |
| | 1.000 | 1 | 2BS | 1 | 1 | 2B | 4RS | 1 | 3BS | 3BS | 3S | 4BS | 5D | 2BS | 2BS | 4BS | 1 |
| | 0.500 | 1 | 1 | 1 | 1 | 1 | 3BS | 1 | 2BS | 2RS | 2S | 3BS | 4BS | 1 | 1 | 3BS | 1 |
| 13 | 4.000 | | | 1 | | 1 | | | 1 | | 1 | 1 | 1 | 1 | | | 1 |
| 14 | 4.000 | | | 1 | | 1 | | | 1 | | 2RS | 2BS | 3RS | 1 | | | 1 |
| 15 | 4.000 | | | 1 | | 2B | | | 5D | | 5D | 5D | 5D | 5D | | | 5D |
| | | | | 2S | | 3BS | | | 5D | | 4BS | 5D | 5D | 5D | | | 3BS |
| | 2.000 | 1 | 2B | 1 | 1 | 1 | 5D | 1 | 4BS | 4RS | 4BS | 4BS | 5D | 4BS | 2BS | 5D | 1 |
| | 1.000 | 1 | 1 | 1 | 1 | 1 | 5D | 1 | 2RS | 4RS | 3RS | 3BS | 5D | 1 | 1 | 1 | 1 |
| | 0.500 | 1 | 1 | 1 | 1 | 1 | 2RS | 1 | 1 | 3RS | 1 | 1 | 4RS | 1 | 1 | 1 | 1 |
| 16 | 4.000 | | | 1 | | 2B | | | 5D | | 5D | 5D | 5D | 5D | | | 2B |
| | 2.000 | 1 | 3BS | 1 | 1 | 1 | 5D | 1 | 5D | 4BS | 3RS | 4BS | 5D | 3BS | 3BS | 3BS | 1 |
| | 1.000 | 1 | 2B | 1 | 1 | 1 | 5D | 1 | 2S | 3RS | 1 | 2BS | 4BS | 1 | 2B | 2S | 1 |
| | 0.500 | 1 | 1 | 1 | 1 | 1 | 3BS | 1 | 1 | 2RS | 1 | 2BS | 2S | 1 | 1 | 1 | 1 |
| 17 | 4.000 | | | 1 | | 1 | | | 1 | | 3RS | 4BS | 5D | 2RS | | | 1 |
| | 2.000 | 1 | 1 | 1 | 1 | 1 | 1 | 1 | 1 | 1 | 1 | 1 | 1 | 1 | 1 | 1 | 1 |
| | 1.000 | 1 | 1 | 1 | 1 | 1 | 1 | 1 | 1 | 1 | 1 | 1 | 1 | 1 | 1 | 1 | 1 |
| | 0.500 | 1 | 1 | 1 | 1 | 1 | 1 | 1 | 1 | 1 | 1 | 1 | 1 | 1 | 1 | 1 | 1 |
| 18 | 4.000 | | | 3BS | | 3BS | | | 5D | | 4BS | 5D | 5D | 5D | | | 4BS |
| | 2.000 | 2BS | 1 | 1 | 1 | 1 | 5N | 1 | 5D | 5D | 5D | 5D | 5D | 4BS | 3BS | 5D | 1 |
| | 1.000 | 2BS | 1 | 1 | 1 | 1 | 5N | 1 | 5D | 5D | 4BS | 4BS | 5D | 4BS | 3BS | 4BS | 1 |
| | 0.500 | 2BS | 1 | 1 | 1 | 1 | 1 | 1 | 4BS | 4BS | 3BS | 4BS | 5D | 2BS | 3BS | 2BS | 1 |
| 19 | 8.000 | | | | | | | | 4BS | | 4BS | | 4BS | | | | |
| | 4.000 | | | 2BS | | 3BS | | | 5D | | 5D | 5D | 5D | 5D | | | 5D |
| | | | | 2S | | 3BS | | | 5D | | 5D | 5D | 5D | 5D | | | 3BS |
| | 2.000 | 1 | 1 | 1 | 1 | 2B | 5D | 1 | 4BS | 5D | 3BS | 5D | 5D | 5D | 3BS | 5D | 1 |
| | 1.000 | 1 | 1 | 1 | 1 | 1 | 5D | 1 | 3BS | 5D | 2S | 4BS | 5D | 4BS | 1 | 5D | 1 |
| | 0.500 | 1 | 1 | 1 | 1 | 1 | 4BS | 1 | 1 | 5D | 1 | 4BS | 5D | 1 | 1 | 4BS | 1 |
| 20 | 8.000 | | | | | | | | 5D | | 4BS | | 5D | | | | |
| | 4.000 | | | 1 | | 1 | | | 5D | | 4BS | 5D | 5D | 5D | | | 4BS |
| | 2.000 | 1 | 2B | 1 | 1 | 1 | 4BS | 1 | 4BS | 5D | 3BS | 3BS | 5D | 2BS | 4BS | 3BS | 1 |
| | 1.000 | 1 | 1 | 1 | 1 | 1 | 2B | 1 | 1 | 1 | 1 | 3BS | 3BS | 1 | 1 | 1 | 1 |
| | 0.500 | 1 | 1 | 1 | 1 | 1 | 1 | 1 | 1 | 1 | 1 | 1 | 1 | 1 | 1 | 1 | 1 |
| 21 | 8.000 | | | | | | | | 5D | | 2S | | 5D | | | | |
| | 4.000 | | | 1 | | 1 | | | 5D | | 2S | 4BS | 5D | 5D | | | 5D |
| | 2.000 | 1 | 1 | 1 | 1 | 1 | 4BS | 1 | 4BS | 5D | 3BS | 4BS | 5D | 2S | 4BS | 3BS | 1 |
| | 1.000 | 1 | 1 | 1 | 1 | 1 | 2BS | 1 | 1 | 1 | 1 | 2BS | 3BS | 1 | 1 | 1 | 1 |
| | 0.500 | 1 | 1 | 1 | 1 | 1 | 1 | 1 | 1 | 1 | 1 | 1 | 1 | 1 | 1 | 1 | 1 |
| 22 | 8.000 | | | | | | | | 5D | | 1 | | 5D | | | | |
| | 4.000 | | | 1 | | 1 | | | 1 | | 1 | 1 | 1 | 1 | | | 1 |
| 23 | 8.000 | | | | | | | | 5D | | 4BS | | 5D | | | | |
| | 4.000 | | | 3BS | | 2BS | | | 5D | | 4BS | 5D | 5D | 4BS | | | 3BS |
| | 2.000 | 1 | 1 | 1 | 1 | 1 | 4BS | 1 | 5D | 5D | 3BS | 4BS | 5D | 2BS | 1 | 3BS | 1 |
| | 1.000 | 1 | 1 | 1 | 1 | 1 | 3BS | 1 | 3BS | 4BS | 1 | 3BS | 5D | 2S | 1 | 1 | 1 |
| | 0.500 | 1 | 1 | 1 | 1 | 1 | 2BS | 1 | 1 | 2BS | 1 | 2BS | 4BS | 1 | 1 | 1 | 1 |
| 24 | 8.000 | | | | | | | | 4RS | | 2RS | | 5D | | | | |
| | 4.000 | | | 1 | | 1 | | | 1 | | 1 | 4BS | 4BS | 1 | | | 1 |
| | 2.000 | 1 | 1 | 1 | 1 | 1 | 1 | 1 | 1 | 1 | 1 | 1 | 1 | 1 | 1 | 1 | 1 |
| | 1.000 | 1 | 1 | 1 | 1 | 1 | 1 | 1 | 1 | 1 | 1 | 1 | 1 | 1 | 1 | 1 | 1 |
| | 0.500 | 1 | 1 | 1 | 1 | 1 | 1 | 1 | 1 | 1 | 1 | 1 | 1 | 1 | 1 | 1 | 1 |
| 25 | 8.000 | | | | | | | | 4BS | | 4RS | | 5D | | | | |
| | 4.000 | | | 1 | | 1 | | | 1 | | 2S | 3BS | 5D | 2S | | | 1 |
| | 2.000 | 1 | 1 | 1 | 1 | 2S | 1 | 1 | 3BS | 1 | 4BS | 4BS | 1 | 1 | 1 | 1 | |
| | 1.000 | 1 | 1 | 1 | 1 | 1 | 1 | 1 | 1 | 1 | 1 | 1 | 1 | 1 | 1 | 1 | |
| | 0.500 | 1 | 1 | 1 | 1 | 1 | 1 | 1 | 1 | 1 | 1 | 1 | 1 | 1 | 1 | 1 | |
| 26 | 8.000 | | | | | | | | 4BS | | 4BS | | 5D | | | | |
| | 4.000 | | | 2C | | 1 | | | 3RCS | | 4BS | 3CBS | 5D | 5D | | | 1 |
| | 2.000 | 1 | 2C | 1 | 1 | 1 | 2RS | 1 | 1 | 4BS | 4BS | 5D | 5D | 3BS | 2BS | 5D | 1 |
| | 1.000 | 1 | 1 | 1 | 1 | 1 | 1 | 1 | 1 | 2BS | 1 | 3BS | 1 | 1 | 1 | 4BS | 1 |
| | 0.500 | 1 | 1 | 1 | 1 | 1 | 1 | 1 | 1 | 1 | 1 | 1 | 1 | 1 | 1 | 1 | 1 |
| 27 | 8.000 | | | | | | | | 5D | | 4BS | | 5D | | | | |
| | 4.000 | | | 2B | | 2B | | | 5D | | 4BS | 5D | 5D | 5D | | | 1 |
| | 2.000 | 1 | 2B | 1 | 1 | 1 | 5N | 1 | 5D | 5D | 5D | 5D | 5D | 4BS | 2BS | 4BS | 1 |
| | 1.000 | 1 | 1 | 1 | 1 | 1 | 5N | 1 | 1 | 4BS | 4BS | 5D | 5D | 3BS | 1 | 3BS | 1 |
| | 0.500 | 1 | 1 | 1 | 1 | 1 | 3RS | 1 | 1 | 4BS | 1 | 4BS | 4BS | 1 | 1 | 1 | 1 |
| | | | 2S | 1 | 1 | 1 | 1 | 1 | 1 | 3BS | 1 | 3BS | 3BS | 1 | 1 | 1 | 1 |
| | 0.250 | 1 | 1 | 1 | 1 | 1 | 1 | 1 | 1 | 1 | 1 | 1 | 1 | 1 | 1 | 1 | 1 |

TABLE III-continued

Preemergence Injury Ratings

| Compound Number | Rate lb/A | A | B | C | D | E | F | G | H | I | J | K | L | M | N | O | P |
|---|---|---|---|---|---|---|---|---|---|---|---|---|---|---|---|---|---|
|  | 0.125 | 1 | 1 | 1 | 1 | 1 | 1 | 1 | 1 | 1 | 1 | 1 | 1 | 1 | 1 | 1 | 1 |
| 28 | 8.000 |  |  |  |  |  |  |  | 0 |  | 0 |  | 0 |  |  |  |  |
|  | 4.000 |  |  | 1 |  | 1 |  |  | 1 |  | 2RS | 1 | 4BS | 1 |  |  | 1 |
| 29 | 8.000 |  |  |  |  |  |  |  | 2B |  | 1 |  | 2BS |  |  |  |  |
|  | 4.000 |  |  | 1 |  | 1 |  |  | 1 |  | 1 | 1 | 1 | 1 |  |  | 1 |
| 30 | 4.000 |  |  | 1 |  | 1 |  |  | 1 |  | 4BS | 1 | 4BS | 3BS |  |  | 1 |
|  | 2.000 | 1 | 2S | 1 | 1 | 1 | 3RS | 2S | 1 | 4RS | 2RS | RS | 4RS | 1 | 1 | 1 | 1 |
|  | 1.000 | 1 | 2S | 1 | 1 | 1 | 2S | 2S | 1 | 2RS | 1 | 2RS | 2S | 1 | 1 | 1 | 1 |
|  | 0.500 | 1 | 1 | 1 | 1 | 1 | 1 | 1 | 1 | 1 | 1 | 1 | 1 | 1 | 1 | 1 | 1 |
| 31 | 4.000 |  |  | 1 |  | 1 |  |  | 1 |  | 1 | 1 | 1 | 1 |  |  | 1 |
| 32 | 8.000 |  |  |  |  |  |  |  | 2C |  | 2RS |  | 4RS |  |  |  |  |
|  | 4.000 |  | 2S |  | 2BS |  |  |  | 2BS |  | 1 | 3BS | 4BS | 2S |  |  | 3S |
| 33 | 8.000 |  |  |  |  |  |  |  | 2CS |  | 3RS |  | 4RS |  |  |  |  |
|  | 4.000 |  | 2S |  | 1 |  |  |  | 4BS |  | 5D | 4BS | 5D | 3BS |  |  | 1 |
|  | 2.000 | 1 | 1 | 1 | 1 | 1 | 1 | 1 | 1 | 3BS | 1 | 1 | 1 | 1 | 1 | 1 | 1 |
|  | 1.000 | 1 | 1 | 1 | 1 | 1 | 1 | 1 | 1 | 2BS | 1 | 1 | 1 | 1 | 1 | 1 | 1 |
|  | 0.500 | 1 | 1 | 1 | 1 | 1 | 1 | 1 | 1 | 1 | 1 | 1 | 1 | 1 | 1 | 1 | 1 |
| 34 | 4.000 |  |  | 1 |  | 1 |  |  | 1 |  | 1 | 1 | 1 | 1 |  |  | 1 |
| 35 | 4.000 |  |  | 1 |  | 1 |  |  | 1 |  | 1 | 1 | 1 | 1 |  |  | 1 |
| 39 | 4.000 |  |  | 1 |  | 1 |  |  | 1 |  | 1 | 1 | 1 | 1 |  |  | 1 |
| 40 | 4.000 |  |  | 1 |  | 1 |  |  | 1 |  | 1 | 1 | 1 |  |  |  | 1 |
| 41 | 8.000 |  |  |  |  |  |  |  | 1 |  | 1 |  | 1 |  |  |  |  |
|  | 4.000 |  |  | 1 |  | 1 |  |  | 2BS |  | 2BS | 3BS | 5D | 1 |  |  | 1 |
|  | 2.000 | 1 | 1 | 1 | 1 | 1 | 1 | 1 | 1 | 2S | 1 | 2S | 2S | 1 | 1 | 2S | 1 |
|  | 1.000 | 1 | 1 | 1 | 1 | 1 | 1 | 1 | 1 | 1 | 1 | 1 | 1 | 1 | 1 | 2S | 1 |
|  | 0.500 | 1 | 1 | 1 | 1 | 1 | 1 | 1 | 1 | 1 | 1 | 1 | 1 | 1 | 1 | 1 | 1 |
| 42 | 8.000 |  |  |  |  |  |  |  | 1 |  | 3RS |  | 2RS |  |  |  |  |
|  | 4.000 |  |  | 1 |  | 1 |  |  | 3RS |  | 4BS | 4BS | 0 | 1 |  |  | 1 |
|  | 2.000 | 1 | 1 | 1 | 1 | 1 | 1 | 1 | 1 | 1 | 1 | 1 | 1 | 1 | 1 | 1 | 1 |
|  | 1.000 | 1 | 1 | 1 | 1 | 1 | 1 | 1 | 1 | 1 | 1 | 1 | 1 | 1 | 1 | 1 | 1 |
|  | 0.500 | 1 | 1 | 1 | 1 | 1 | 1 | 1 | 1 | 1 | 1 | 1 | 1 | 1 | 1 | 1 | 1 |
| 43 | 4.000 |  |  | 1 |  | 1 |  |  | 1 |  | 1 | 1 | 1 | 1 |  |  | 1 |
| 44 | 8.000 |  |  |  |  |  |  |  | 2BS |  | 2S |  | 5D |  |  |  |  |
|  | 4.000 |  |  | 1 |  | 1 |  |  | 2BS |  | 4SF | 1 | 5D | 1 |  |  | 0 |
|  | 2.000 | 2S | 1 | 1 | 1 | 1 | 3BS | 1 | 2S | 2RS | 1 | 2CS | 3RS | 3RS | 1 | 1 | 1 |
|  | 1.000 | 2S | 1 | 1 | 1 | 1 | 2BS | 1 | 1 | 1 | 1 | 1 | 1 | 2RS | 1 | 1 | 1 |
|  | 0.500 | 1 | 1 | 1 | 1 | 1 | 1 | 1 | 1 | 1 | 1 | 1 | 1 | 1 | 1 | 1 | 1 |
| 45 | 8.000 |  |  |  |  |  |  |  | 0 |  | 0 |  | 0 |  |  |  |  |
|  | 4.000 |  |  | 1 |  | 1 |  |  | 1 |  | 1 | 1 | 1 | 1 |  |  | 1 |
| 46 | 4.000 |  |  | 1 |  | 1 |  |  | 4BS |  | 4RS | 4BS | 5D | 5D |  |  | 1 |
|  | 2.000 | 1 | 1 | 1 | 1 | 1 | 3RS | 1 | 1 | 3RS | 2RS | 4BS | 4BS | 1 | 1 | 1 | 1 |
|  | 1.000 | 1 | 1 | 1 | 1 | 1 | 1 | 1 | 1 | 2RS | 1 | 2BS | 2BS | 1 | 1 | 1 | 1 |
|  | 0.500 | 1 | 1 | 1 | 1 | 1 | 1 | 1 | 1 | 1 | 1 | 1 | 1 | 1 | 1 | 1 | 1 |
| 47 | 8.000 |  |  |  |  |  |  |  | 3SF |  | 2S |  | 4BS |  |  |  |  |
|  | 4.000 |  |  | 1 |  | 1 |  |  | 1 |  | 1 | 3RBS | 4RS | 2S |  |  | 1 |
| 48 | 4.000 |  |  | 1 |  | 1 |  |  | 2S |  | 2S | 3BS | 3RS | 2RS |  |  | 1 |
| 49 | 4.000 |  |  | 1 |  | 1 |  |  | 4BS |  | 3RS | 4BS | 5D | 2RS |  |  | 1 |
|  | 2.000 | 1 | 1 | 1 | 1 | 1 | 4BS | 1 | 2BS | 5D | 1 | 3BS | 4BS | 1 | 1 | 2BS | 1 |
|  | 1.000 | 1 | 1 | 1 | 1 | 1 | 3BS | 1 | 2S | 1 | 1 | 2BS | 3BS | 1 | 1 | 1 | 1 |

We claim:

1. A compound of the formula (1)

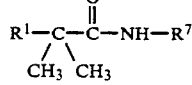

(1)

wherein R$^1$ is

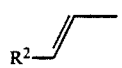

(a)

(E)

where R$^2$ is F, Cl, Br, I, SCH$_3$, or OCH$_3$,

(b)

(Z)

(c)

where R$^3$ is F, Cl, or Br,

(d)

where R$^4$ and R$^5$ are both Cl or both Br, or

(e)

(Z)

where R$^6$ is F, Cl, or Br; and

R$^7$ is

-continued

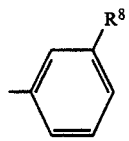

where $R^8$ is H, F, Cl, Br, I, SCF$_3$, or CF$_3$,

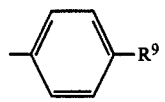

where $R^9$ is F, Cl, Br, I, SCF$_3$, SOCF$_3$, SO$_2$CF$_3$, halo (C$_1$-C$_3$) alkyl, (C$_1$-C$_3$) alkoxy, halo (C$_1$-C$_3$) alkoxy,

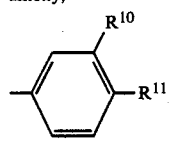

where $R^{10}$ and $R^{11}$ are independently F, Cl, Br, SCH$_3$, or CF$_3$; or

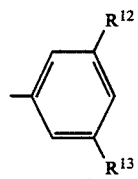

where $R^{12}$ and $R^{13}$ are both F or both Cl.

2. A compound of claim 1 wherein $R^1$ is

3. A compound of claim 2 wherein $R^7$ is 4-fluorophenyl, 4-chlorophenyl, or 4-bromophenyl.

4. A compound of claim 2 wherein $R^7$ is 3,4-difluorophenyl, 3,5-difluorophenyl, 3-chloro-4-fluorophenyl, 3,4-dichlorophenyl, or 3-fluoro-4-chlorophenyl.

5. A compound of claim 2 wherein $R^7$ is 4-(trifluoromethyl)phenyl, 4-[(trifluoromethyl)thio]phenyl, or 4-[(trifluoromethyl)sulfinyl]phenyl.

6. A compound of claim 1 wherein $R^1$ is (a) 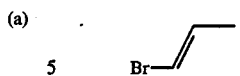

7. A compound of claim 6 wherein $R^7$ is 4-fluorophenyl, 4-chlorophenyl, or 4-bromophenyl.

8. A compound of claim 6 wherein $R^7$ is 3,4-difluorophenyl, 3,5-difluorophenyl, 3-chloro-4-fluorophenyl, 3,4-dichlorophenyl, or 3-fluoro-4-chlorophenyl.

9. A compound of claim 6 wherein $R^7$ is 4-(trifluoromethyl)phenyl, 4-[(trifluoromethyl)thio]phenyl, or 4-[(trifluoromethyl)sulfinyl]phenyl.

10. A compound of claim 1 wherein $R^1$ is (c) 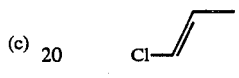

11. A compound of claim 10 wherein $R^7$ is 4-fluorophenyl, 4-chlorophenyl, or 4-bromophenyl.

12. The compound of claim 11 which is (E)-4-chloro-N-(4-chlorophenyl)-2,2-dimethyl-3-butenamide.

13. A compound of claim 10 wherein $R^7$ is 3,4-difluorophenyl, 3,5-difluorophenyl, 3-chloro-4-fluorophenyl, 3,4-dichlorophenyl, or 3-fluoro-4-chlorophenyl.

14. A compound of claim 10 wherein $R^7$ is 4-(trifluoromethyl)phenyl, 4-[(trifluoromethyl)thio]phenyl, or 4-[(trifluoromethyl)sulfinyl]phenyl.

15. A herbicide composition comprising as active ingredient a compound of claim 1 in combination with an agriculturally acceptable carrier.

16. A compound of claim 13 wherein $R^1$ is

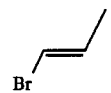

17. A compound of claim 13 wherein $R^1$ is

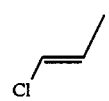

* * * * *